US008372955B2

(12) United States Patent
Viellard et al.

(10) Patent No.: US 8,372,955 B2
(45) Date of Patent: Feb. 12, 2013

(54) PURIFIED ANTIBODY TO THE EXTRACELLULAR DOMAIN OF NKP44L

(75) Inventors: Vincent Viellard, Paris (FR); Patrice Debre, Paris (FR)

(73) Assignees: Assistance Publique Hopitaux de Paris, Paris (FR); Institut National de la Sante et de la Recherche Medicale (INSERM), Paris (FR)

( * ) Notice: Subject to any disclaimer, the term of this patent is extended or adjusted under 35 U.S.C. 154(b) by 38 days.

(21) Appl. No.: 11/927,400

(22) Filed: Oct. 29, 2007

(65) Prior Publication Data

US 2009/0117110 A1 May 7, 2009

Related U.S. Application Data

(62) Division of application No. 10/544,884, filed as application No. PCT/EP2004/001106 on Feb. 6, 2004, now abandoned.

(30) Foreign Application Priority Data

Feb. 6, 2003 (EP) .................................. 03290303

(51) Int. Cl.
*A61K 39/395* (2006.01)
*A61K 39/00* (2006.01)
*C07K 16/08* (2006.01)

(52) U.S. Cl. ............... 530/387.1; 424/130.1; 424/135.1; 424/139.1; 424/141.1

(58) Field of Classification Search .................. None
See application file for complete search history.

(56) References Cited

U.S. PATENT DOCUMENTS

2009/0203885 A1* 8/2009 Fisher et al. ................. 530/350

FOREIGN PATENT DOCUMENTS

| CA | 2431881 | 7/2002 |
|---|---|---|
| WO | WO 98/20036 | 5/1998 |
| WO | WO 01/55322 | * 8/2001 |
| WO | WO 01/79291 | * 10/2001 |
| WO | WO 02/08287 | * 1/2002 |
| WO | WO 02/053587 | 7/2002 |

OTHER PUBLICATIONS

Alignment for WO 01/79291.*
Alignment for WO 01/55322.*
The Illustrated Dictionary of Immunology (1995, CRC Press, Inc. Boca Raton FL; JM Cruse and RE Lewis eds.).*
Chen et al., "Monoclonal antibodies that bind to the core of fusion-active glycoprotein 41," *AIDS Research and Human Retroviruses*, 16(18):2037-2041, 2000.
Emerling et al., "MLL5, a homolog of *Drosophila* trithorax located within a segment of chromosome band 7q22 implicated in myeloid leukemia," *Oncogene*, 21:4849-4854, 2002.
Human Immunodeficiency virus, GenBank Accession No. AAN31566, 2002.
Mwaengo and Novembre, "Molecular cloning and characterization of viruses isolated from chimpanzees with pathogenic human immunodeficiency virus type 1 infections," *Journal of Virology*, 72(11):8976-8987, 1998.
Ryu et al., "Development of an in vitro assay system for screening of gp41 inhibitory compounds," *Mol. Cells*, 8(6):717-723, 1998.
Viellard et al., "NK cytoxicity against CD4+ cells during HIV-1 expression of an NKp44 ligand," *Proc. Natl. Acad. Sci. USA*, 102:10891-10986, 2005.

* cited by examiner

*Primary Examiner* — Zachariah Lucas
*Assistant Examiner* — Nicole Kinsey White
(74) *Attorney, Agent, or Firm* — Fulbright & Jaworski L.L.P.

(57) ABSTRACT

The present invention relates to the field of the in vitro diagnosis of the progression status of an infection of an individual with a virus belonging to the family of the Human Immunodeficiency Viruses (HIV) as well as with the therapeutical treatment of this infectious disease.

5 Claims, 19 Drawing Sheets

NKp44L expression

NKp44L expression

A

WT : NH2-PWASNA-SWSNKS-LDDIW-COOH
ctl1 : NH2-PWASNA-TWTQRT-LDDIW-COOH
ctl2 : NH2-PWGTQG-TWTQRT-IEELW-COOH

B

C

SEQUENCE LISTING

```
<160> NUMBER OF SEQ ID NOS: 6

<210> SEQ ID NO 1
<211> LENGTH: 1168
<212> TYPE: PRT
<213> ORGANISM: Homo sapiens

<400> SEQUENCE: 1

Met Ser Ile Val Ile Pro Leu Gly Val Asp Thr Ala Glu Thr Ser Tyr
 1               5                  10                  15

Leu Glu Met Ala Ala Gly Ser Glu Pro Glu Ser Val Glu Ala Ser Pro
            20                  25                  30

Val Val Val Glu Lys Ser Asn Ser Tyr Pro His Gln Leu Tyr Thr Ser
        35                  40                  45

Ser Ser His His Ser His Ser Tyr Ile Gly Leu Pro Tyr Ala Asp His
    50                  55                  60

Asn Tyr Gly Ala Arg Pro Pro Pro Thr Pro Pro Ala Ser Pro Pro Pro
65                  70                  75                  80

Ser Val Leu Ile Ser Lys Asn Glu Val Gly Ile Phe Thr Thr Pro Asn
                85                  90                  95

Phe Asp Glu Thr Ser Ser Ala Thr Thr Ile Ser Thr Ser Glu Asp Gly
            100                 105                 110

Ser Tyr Gly Thr Asp Val Thr Arg Cys Ile Cys Gly Phe Thr His Asp
        115                 120                 125

Asp Gly Tyr Met Ile Cys Cys Asp Lys Cys Ser Val Trp Gln His Ile
    130                 135                 140

Asp Cys Met Gly Ile Asp Arg Gln His Ile Pro Asp Thr Tyr Leu Cys
145                 150                 155                 160

Glu Arg Cys Gln Pro Arg Asn Leu Asp Lys Glu Arg Ala Val Leu Leu
                165                 170                 175

Gln Arg Arg Lys Arg Glu Asn Met Ser Asp Gly Asp Thr Ser Ala Thr
            180                 185                 190

Glu Ser Gly Asp Glu Val Pro Val Glu Leu Tyr Thr Ala Phe Gln His
        195                 200                 205

Thr Pro Thr Ser Ile Thr Leu Thr Ala Ser Arg Val Ser Lys Val Asn
    210                 215                 220

Asp Lys Arg Arg Lys Lys Ser Gly Glu Lys Glu Gln His Ile Ser Lys
225                 230                 235                 240

Cys Lys Lys Ala Phe Arg Glu Gly Ser Arg Lys Ser Ser Arg Val Lys
                245                 250                 255
```

```
Gly Ser Ala Pro Glu Ile Asp Pro Ser Ser Asp Gly Ser Asn Phe Gly
            260                 265                 270

Trp Glu Thr Lys Ile Lys Ala Trp Met Asp Arg Tyr Glu Glu Ala Asn
            275                 280                 285

Asn Asn Gln Tyr Ser Glu Gly Val Gln Arg Glu Ala Gln Arg Ile Ala
            290                 295                 300

Leu Arg Leu Gly Asn Gly Asn Asp Lys Lys Glu Met Asn Lys Ser Asp
305                 310                 315                 320

Leu Asn Thr Asn Asn Leu Leu Phe Lys Pro Pro Val Glu Ser His Ile
                325                 330                 335

Gln Lys Asn Lys Lys Ile Leu Lys Ser Ala Lys Asp Leu Pro Pro Asp
                340                 345                 350

Ala Leu Ile Ile Glu Tyr Arg Gly Lys Phe Met Leu Arg Glu Gln Phe
                355                 360                 365

Glu Ala Asn Gly Tyr Phe Phe Lys Arg Pro Tyr Pro Phe Val Leu Phe
            370                 375                 380

Tyr Ser Lys Phe His Gly Leu Glu Met Cys Val Asp Ala Arg Thr Phe
385                 390                 395                 400

Gly Asn Glu Ala Arg Phe Ile Arg Arg Ser Cys Thr Pro Asn Ala Glu
                405                 410                 415

Val Arg His Glu Ile Gln Asp Gly Thr Ile His Leu Tyr Ile Tyr Ser
                420                 425                 430

Ile His Ser Ile Pro Lys Gly Thr Glu Ile Thr Ile Ala Phe Asp Phe
                435                 440                 445

Asp Tyr Gly Asn Cys Lys Tyr Lys Val Asp Cys Ala Cys Leu Lys Glu
            450                 455                 460

Asn Pro Glu Cys Pro Val Leu Arg Ser Ser Glu Ser Met Glu Asn
465                 470                 475                 480

Ile Asn Ser Gly Tyr Glu Thr Arg Arg Lys Gly Lys Lys Asp Glu
                485                 490                 495

Asp Ile Ser Lys Glu Lys Asp Thr Gln Asn Gln Asn Ile Thr Leu Asp
                500                 505                 510

Cys Glu Gly Ala Thr Asn Lys Met Lys Ser Pro Glu Thr Lys Gln Arg
            515                 520                 525

Lys Leu Ser Pro Leu Arg Leu Ser Val Ser Asn Asn Gln Glu Pro Asp
            530                 535                 540

Phe Ile Asp Asp Ile Glu Glu Lys Thr Pro Ile Ser Asn Glu Val Glu
545                 550                 555                 560

Met Glu Ser Glu Glu Gln Ile Ala Glu Arg Lys Arg Lys Met Thr Arg
                565                 570                 575

Glu Glu Arg Lys Met Glu Ala Ile Leu Gln Ala Phe Ala Arg Leu Glu
            580                 585                 590

Lys Arg Glu Lys Arg Arg Glu Gln Ala Leu Glu Arg Ile Ser Thr Ala
            595                 600                 605

Lys Thr Glu Val Lys Thr Glu Cys Lys Asp Thr Gln Ile Val Ser Asp
            610                 615                 620

Ala Glu Val Ile Gln Glu Gln Ala Lys Glu Glu Asn Ala Ser Lys Pro
625                 630                 635                 640

Thr Pro Ala Lys Val Asn Arg Thr Lys Gln Arg Lys Ser Phe Ser Arg
                645                 650                 655

Ser Arg Thr His Ile Gly Gln Gln Arg Arg His Arg Thr Val Ser
            660                 665                 670

Met Cys Ser Asp Ile Gln Pro Ser Ser Pro Asp Ile Glu Val Thr Ser
```

```
            675                 680                 685
Gln Gln Asn Asp Ile Glu Asn Thr Val Leu Thr Ile Glu Pro Glu Thr
            690                 695                 700
Glu Thr Ala Leu Ala Glu Ile Ile Thr Glu Thr Glu Val Pro Ala Leu
705                 710                 715                 720
Asn Lys Cys Pro Thr Lys Tyr Pro Lys Thr Lys Lys His Leu Val Asn
            725                 730                 735
Glu Trp Leu Ser Glu Lys Asn Glu Lys Thr Gly Lys Pro Ser Asp Gly
            740                 745                 750
Leu Ser Glu Arg Pro Leu Arg Ile Thr Thr Asp Pro Glu Val Leu Ala
            755                 760                 765
Thr Gln Leu Asn Ser Leu Pro Gly Leu Thr Tyr Ser Pro His Val Tyr
            770                 775                 780
Ser Thr Pro Lys His Tyr Ile Arg Phe Thr Ser Pro Phe Leu Ser Glu
785                 790                 795                 800
Lys Arg Arg Arg Lys Glu Pro Thr Glu Asn Ile Ser Gly Ser Cys Lys
            805                 810                 815
Lys Arg Trp Leu Lys Gln Ala Leu Glu Glu Asn Ser Ala Ile Leu
            820                 825                 830
His Arg Phe Asn Ser Pro Cys Gln Glu Arg Ser Arg Ser Pro Ala Val
            835                 840                 845
Asn Gly Glu Asn Lys Ser Pro Leu Leu Leu Asn Asp Ser Cys Ser Leu
            850                 855                 860
Pro Asp Leu Thr Thr Pro Leu Lys Lys Arg Arg Phe Tyr Gln Leu Leu
865                 870                 875                 880
Asp Ser Val Tyr Ser Glu Thr Ser Thr Pro Thr Pro Ser Pro Tyr Ala
            885                 890                 895
Thr Pro Thr His Thr Asp Ile Thr Pro Met Asp Pro Ser Phe Ala Thr
            900                 905                 910
Pro Pro Arg Ile Lys Ser Asp Asp Glu Thr Cys Arg Asn Gly Tyr Lys
            915                 920                 925
Pro Ile Tyr Ser Pro Val Thr Pro Val Thr Pro Gly Thr Pro Gly Asn
            930                 935                 940
Thr Met His Phe Glu Asn Ile Ser Ser Pro Glu Ser Ser Pro Glu Ile
945                 950                 955                 960
Lys Arg Arg Thr Tyr Ser Gln Glu Gly Tyr Asp Arg Ser Ser Thr Met
            965                 970                 975
Leu Thr Leu Gly Pro Phe Arg Asn Ser Asn Leu Thr Glu Leu Gly Leu
            980                 985                 990
Gln Glu Ile Lys Thr Ile Gly Tyr Thr Ser Pro Arg Ser Arg Thr Glu
            995                 1000                1005
Val Asn Arg Gln Cys Pro Gly Glu Lys Glu Pro Val Ser Asp Leu Gln
    1010                1015                1020
Leu Gly Leu Asp Ala Val Glu Pro Thr Ala Leu His Lys Thr Leu Glu
    1025                1030                1035                1040
Thr Pro Ala His Asp Arg Ala Glu Pro Asn Ser Gln Leu Asp Ser Thr
            1045                1050                1055
His Ser Gly Arg Gly Thr Met Tyr Ser Ser Trp Val Lys Ser Pro Asp
            1060                1065                1070
Arg Thr Gly Val Asn Phe Ser Val Asn Ser Asn Leu Arg Asp Leu Thr
            1075                1080                1085
Pro Ser His Gln Leu Glu Val Gly Gly Gly Phe Arg Ile Ser Glu Ser
        1090                1095                1100
```

Lys Cys Leu Met Gln Asp Asp Thr Arg Gly Met Phe Met Glu Thr Thr
1105                1110                1115                1120

Val Phe Cys Thr Ser Glu Asp Gly Leu Val Ser Gly Phe Gly Arg Thr
            1125                1130                1135

Val Asn Asp Asn Leu Ile Asp Gly Asn Cys Thr Pro Gln Asn Pro Pro
        1140                1145                1150

Gln Lys Lys Lys Ser Pro Val Gly Asn Phe Val Gly Ser Asn Val Val
    1155                1160                1165

<210> SEQ ID NO 2
<211> LENGTH: 262
<212> TYPE: PRT
<213> ORGANISM: Homo sapiens

<400> SEQUENCE: 2

Met Ala Trp Arg Ala Leu His His Trp Leu Leu Leu Leu Phe Pro
 1               5                  10                  15

Gly Ser Gln Ala Gln Ser Lys Ala Gln Val Leu Gln Ser Val Ala Gly
            20                  25                  30

Gln Thr Leu Thr Val Arg Cys Gln Tyr Pro Pro Thr Gly Ser Leu Tyr
        35                  40                  45

Glu Lys Lys Gly Trp Cys Lys Glu Ala Ser Ala Leu Val Cys Ile Arg
    50                  55                  60

Leu Val Thr Ser Ser Lys Pro Arg Thr Met Ala Trp Thr Ser Arg Phe
65                  70                  75                  80

Thr Ile Trp Asp Asp Pro Asp Ala Gly Phe Phe Thr Val Thr Met Thr
                85                  90                  95

Asp Leu Arg Glu Glu Asp Ser Gly His Tyr Trp Cys Arg Ile Tyr Arg
            100                 105                 110

Pro Ser Asp Asn Ser Val Ser Lys Ser Val Arg Phe Tyr Leu Val Val
        115                 120                 125

Ser Pro Ala Ser Ala Ser Thr Gln Thr Pro Trp Thr Pro Arg Asp Leu
130                 135                 140

Val Ser Ser Gln Thr Gln Thr Gln Ser Cys Val Pro Pro Thr Ala Gly
145                 150                 155                 160

Ala Arg Gln Ala Pro Glu Ser Pro Ser Thr Ile Pro Val Pro Ser Gln
                165                 170                 175

Pro Gln Asn Ser Thr Leu Arg Pro Gly Pro Ala Ala Pro Ile Ala Leu
            180                 185                 190

Val Pro Val Phe Cys Gly Leu Leu Val Ala Lys Ser Leu Val Leu Ser
        195                 200                 205

Ala Leu Leu Val Trp Trp Gly Asp Ile Trp Trp Lys Thr Val Met Glu
210                 215                 220

Leu Arg Ser Leu Asp Thr Gln Lys Ala Thr Cys His Leu Gln Gln Val
225                 230                 235                 240

Thr Asp Leu Pro Trp Thr Ser Val Ser Ser Pro Val Glu Arg Glu Ile
                245                 250                 255

Leu Tyr His Thr Val Ala
            260

<210> SEQ ID NO 3
<211> LENGTH: 3507
<212> TYPE: DNA
<213> ORGANISM: Homo sapiens

<400> SEQUENCE: 3
atgagcatag tgatcccatt gggggttgat acagcagaga cgtcatactt ggaaatggct      60

| | |
|---|---|
| gcaggttcag aaccagaatc cgtagaagct agccctgtgg tagttgagaa atccaacagt | 120 |
| tatccccacc agttatatac cagcagctca catcattcac acagttacat tggtttgccc | 180 |
| tatgcggacc ataattatgg tgctcgtcct cctccgacac ctccggcttc ccctcctcca | 240 |
| tcagtcctta ttagcaaaaa tgaagtaggc atatttacca ctcctaattt tgatgaaact | 300 |
| tccagtgcta ctacaatcag cacatctgag gatggaagtt atggtactga tgtaaccagg | 360 |
| tgcatatgtg gttttacaca tgatgatgga tacatgatct gttgtgacaa atgcagcgtt | 420 |
| tggcaacata ttgactgcat ggggattgat aggcagcata ttcctgatac atatctatgt | 480 |
| gaacgttgtc agcctaggaa tttggataaa gagagggcag tgctactaca acgccggaaa | 540 |
| agggaaaata tgtcagatgg tgataccagt gcaactgaga gtggtgatga ggttcctgtg | 600 |
| gaattatata ctgcatttca gcatactcca acatcaatta ctttaactgc ttcaagagtt | 660 |
| tccaaagtta atgataaaag aaggaaaaaa agcggggaga agaacaaca catttcaaaa | 720 |
| tgtaaaaagg catttcgtga aggatctagg aagtcatcaa gagttaaggg ttcagctcca | 780 |
| gagattgatc cttcatctga tggttcaaat tttggatggg agacaaagat caaagcatgg | 840 |
| atggatcgat atgaagaagc aaataacaac cagtatagtg agggtgttca gagggaggca | 900 |
| caaagaatag ctctgagatt aggcaatgga aatgacaaaa aagagatgaa taaatccgat | 960 |
| ttgaatacca acaatttgct cttcaaacct cctgtagaga gccatataca aaagaataag | 1020 |
| aaaattctta aatctgcaaa agatttgcct cctgatgcac ttatcattga atacagaggg | 1080 |
| aagtttatgc tgagagaaca gtttgaagca aatgggtatt tctttaaaag accatacct | 1140 |
| tttgtgttat tctactctaa atttcatggg ctagaaatgt gtgttgatgc aaggactttt | 1200 |
| gggaatgagg ctcgattcat caggcggtct tgtacaccca atgcagaggt gaggcatgaa | 1260 |
| attcaagatg gaaccataca tctttatatt tattctatac acagtattcc aaagggaact | 1320 |
| gaaattacta ttgcctttga ttttgactat ggaaattgta agtacaaggt ggactgtgca | 1380 |
| tgcctcaaag aaaacccaga gtgccctgtt ctaaaacgta gttctgaatc catggaaaat | 1440 |
| atcaatagtg gttatgagac cagacggaaa aaggaaaaa aagacgaaga tatttcaaaa | 1500 |
| gaaaaagata cacaaaatca gaatattact ttggattgtg aaggagcgac caacaaaatg | 1560 |
| aagagcccag aaactaaaca aagaaagctt tctccactga gactatcagt atcaaataat | 1620 |
| caggaaccag attttattga tgatatagaa gaaaaaactc ctattagtaa tgaagtagaa | 1680 |
| atggaatcag aggagcagat tgcagaaagg aaaaggaaga tgacaagaga agaaagaaaa | 1740 |
| atggaagcaa ttttgcaagc ttttgccaga cttgaaaaaa gagagaaaag aagagaacaa | 1800 |
| gctttggaaa ggatcagcac agccaaaact gaagttaaaa ctgaatgtaa agatacacag | 1860 |
| attgtcagtg atgctgaagt tattcaggaa caagcaaaag aagaaatgc tagcaagcca | 1920 |
| accctgcca agtaaatag aactaaacag agaaaaagtt tttctcggag taggactcac | 1980 |
| attggacagc agcgtcggag acacagaact gtcagcatgt gttcagatat ccagccatct | 2040 |
| tctcctgata tagaagttac ttcacaacaa aatgatattg aaaatactgt acttacaata | 2100 |
| gaaccagaaa ctgaaactgc actagcagaa ataattactg aaactgaagt tccagcactt | 2160 |
| aataaatgtc ctaccaagta ccccaaaaca aagaagcact tggttaatga atggttaagt | 2220 |
| gagaagaatg agaagacagg aaaaccttca gatggccttt cagaaaggcc tctacgcata | 2280 |
| actacagatc ctgaagtgtt agctacacaa ctcaattctt taccaggtct cacttacagc | 2340 |
| ccccatgtat actccactcc taagcattat attagattta cttcaccatt cctttcgaaa | 2400 |
| aaaggagaa gaaaagaacc tactgaaaac atttctggtt catgcaagaa gcgatggttg | 2460 |

```
aaacaagctc tggaagaaga aaattcagca attttacata gatttaattc accctgtcaa    2520
gaaagatcca gaagtcctgc agtcaatggt gaaaataaaa gtccactact attaaatgac    2580
agctgttccc ttccagattt aactacacca ctaaaaaaac gaagatttta tcagttgcta    2640
gattcggttt actcagaaac ctccacacct actccttccc cgtatgctac accaactcac    2700
accgatatta ctcctatgga cccatctttt gccacgcctc cacggataaa atcagatgat    2760
gaaacttgta gaaatggtta taaacccata tattcaccag ttaccccagt aactcctggt    2820
acaccaggaa ataccatgca ctttgagaat atttcttccc cagaaagttc tccagaaata    2880
aagagacgca cttatagtca agagggatat gacagatctt caaccatgtt aacattgggg    2940
ccttttagaa attctaattt aactgaactg ggtctgcaag aaataaagac tattggttat    3000
acgagcccta ggagtaggac tgaagtcaac aggcagtgtc ctggagaaaa ggaacctgtg    3060
tcagaccttc agctaggact cgatgcagtt gagccaactg ccctacataa aaccctggaa    3120
acgcctgcac atgacagggc tgagcccaac agccaactgg actcgactca ctctggacgg    3180
ggcacaatgt attcttcctg ggtaaagagc cctgacagaa caggagttaa cttctcagtg    3240
aactccaact tgagggacct gacaccctcg catcagttgg aggttggagg aggcttccga    3300
ataagtgagt caaagtgcct gatgcaggat gatactagag gcatgtttat ggaaacaact    3360
gtgttttgta cttccgaaga tgggcttgta tctggtttcg gacggactgt taatgacaat    3420
ttgatcgacg ggaattgcac accccagaat ccaccacaaa agaaaaagag tccagttggc    3480
aactttgtgg gaagcaatgt agtatag                                        3507

<210> SEQ ID NO 4
<211> LENGTH: 787
<212> TYPE: DNA
<213> ORGANISM: Homo sapiens

<400> SEQUENCE: 4
atggcctggc gagccctaca ccactggcta ctgctgctgc tgttcccagg ctctcaggca      60
caatccaagg ctcaggtact tcaaagtgtg gcagggcaga cgctaaccgt gagatgccag     120
tacccgccca cgggcagtct ctacgagaag aaaggctggt gtaaggaggc ttcagcactt     180
gtgtgcatca ggttagtcac cagctccaag cccaggacga tggcttggac ctctcgattc     240
acaatctggg acgaccctga tgctggcttc ttcactgtca ccatgactga tctaagagag     300
gaagactcag acattactg tgtagaatc taccgcccctt ctgacaactc tgtctctaag     360
tccgtcagat tctatctggt ggtatctcca gcctctgcct ccacacagac cccctggact     420
ccccgcgacc tggtctcttc acagaccag cccagagct gtgtgcctcc cactgcagga      480
gccagacaag cccctgagtc tccatctacc atccctgtcc cttctcagcc acagaactcc     540
acgctccgcc ctggccctgc agcccccatt gccctggtgc ctgtgttctg tggactcctc     600
gtagccaaga gcctggtgct gtcagccctg ctcgtctggt gggggacat atggtggaaa     660 accgtgatgg agctcaggag cctggatacc caaaaagcca cctgccacct tcaacaggtc     720
acggaccttc cctggacctc agtttcctca cctgtagaga gagaaatatt atatcacact     780
gttgcaa                                                               787

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
        Peptide
<220> FEATURE:
<221> NAME/KEY: MOD_RES
<222> LOCATION: (1)..(3)
<223> OTHER INFORMATION: X = any amino acid
<220> FEATURE:
<221> NAME/KEY: MOD_RES
<222> LOCATION: (4)
<223> OTHER INFORMATION: X = any amino acid residue except A and W
<220> FEATURE:
<221> NAME/KEY: MOD_RES
<222> LOCATION: (5)..(6)
<223> OTHER INFORMATION: X = any amino acid
<220> FEATURE:
<221> NAME/KEY: MOD_RES
<222> LOCATION: (13)
<223> OTHER INFORMATION: X = any amino acid
<220> FEATURE:
<221> NAME/KEY: MOD_RES
<222> LOCATION: (14)
<223> OTHER INFORMATION: X = any amino acid residue except E and S
<220> FEATURE:
<221> NAME/KEY: MOD_RES
<222> LOCATION: (15)..(17)
<223> OTHER INFORMATION: X = any amino acid

<400> SEQUENCE: 5

Xaa Xaa Xaa Xaa Xaa Xaa Ser Trp Ser Asn Lys Ser Xaa Xaa Xaa Xaa
 1               5                  10                  15

Xaa

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Pro Trp Ala Ser Asn Ala Ser Trp Ser Asn Lys Ser Leu Asp Asp Ile
 1               5                  10                  15

Trp
```

PURIFIED ANTIBODY TO THE EXTRACELLULAR DOMAIN OF NKP44L

This application is a divisional of U.S. application Ser. No. 10/544,884 filed 17 May 2006, now abandoned, which is a national phase application under 35 U.S.C. §371 of International Application No. PCT/EP2004/001106 filed 6 Feb. 2004, which claims priority to European Application No. 03290303.1 filed 6 Feb. 2003. The entire text of each of the above-referenced disclosures is specifically incorporated herein by reference without disclaimer.

FIELD OF THE INVENTION

The present invention relates to the field of the in vitro diagnosis of the progression status of an infection of an individual with a virus belonging to the family of the Human Immunodeficiency Viruses (HIV) as well as with the therapeutical treatment of this infectious disease.

BACKGROUND OF THE INVENTION

AIDS disease, which is primarily caused by infection of individuals with a HIV retrovirus, is now the most devastating disease in the whole world, since the number of individuals which are, to date, infected with HIV viruses is estimated to about 40 millions of individuals.

During the sole year 2001, 5 millions of individuals were infected with HIV while 3 millions of individuals have deceased in the same time. Since the discovery of the main AIDS causative agent in 1983, namely the HIV virus, extensive efforts have been made in order to understand the mechanism of action of this virus and to develop accurate methods for (i) reproducibly diagnosing the infection, as well as (ii) carrying out a prognosis of the progression of the disease in a given patient.

For surveillance purposes, the United States Centers for Disease Control (CDC) currently defines AIDS in an adult or adolescent age 13 years or older as the presence of one of 25 AIDS-indicator conditions, such as KS, PCP or disseminated MAC. In children younger than 13 years, the definition of AIDS is similar to that in adolescents and adults, except that lymphoid interstitial pneumonitis and recurrent bacterial infections are included in the list of AIDS-defining conditions (CDC, 1987b). The case definition in adults and adolescents was expanded in 1993 to include HIV infection in an individual with a CD4$^+$ T cell count less than 200 cells per cubic millimeter (mm$^3$) of blood (CDC, 1992). The current surveillance definition replaced criteria published in 1987 that were based on clinical conditions and evidence of HIV infection but not on CD4$^+$ T cell determinations (CDC, 1987).

In clinical practice, symptomatology and measurements of immune function, notably levels of CD4$^+$ T lymphocytes, are used to guide the treatment of HIV-infected persons.

HIV infects and kills CD4$^+$ T lymphocytes in vitro, although scientists have developed immortalized T-cell lines in order to propagate HIV in the laboratory (Popovic et al., 1984; Zagury et al., 1986; Garry, 1989; Clark et al., 1991). Several mechanisms of CD4$^+$ T cell killing have been observed in lentivirus systems in vitro and may explain the progressive loss of these cells in HIV-infected individuals (reviewed in Garry, 1989; Fauci, 1993a; Pantaleo et al., 1993a). These mechanisms include disruption of the cell membrane as HIV buds from the surface (Leonard et al., 1988) or the intracellular accumulation of heterodisperse RNAs and unintegrated DNA (Pauza et al., 1990; Koga et al., 1988). Evidence also suggests that intracellular complexing of CD4 and viral envelope products can result in cell killing (Hoxie et al., 1986).

In addition to these direct mechanisms of CD4$^+$ T cell depletion, indirect mechanisms may result in the death of uninfected CD4$^+$ T cells (reviewed in Fauci, 1993a; Pantaleo et al., 1993a). Uninfected cells often fuse with infected cells, resulting in giant cells called syncytia that have been associated with the cytopathic effect of HIV in vitro (Sodroski et al., 1986; Lifson et al., 1986). Uninfected cells also may be killed when free gp120, the envelope protein of HIV, binds to their surfaces, marking them for destruction by antibody-dependent cellular cytotoxicity responses (Lyerly et al., 1987). Other autoimmune phenomena may also contribute to CD4$^+$ T cell death since HIV envelope proteins share some degree of homology with certain major histocompatibility complex type II (MHC-II) molecules (Golding et al., 1989; Koenig et al., 1988).

A number of investigators have suggested that superantigens, either encoded by HIV or derived from unrelated agents, may trigger massive stimulation and expansion of CD4$^+$ T cells, ultimately leading to depletion or anergy of these cells (Janeway, 1991; Hugin et al., 1991). The untimely induction of a form of programmed cell death called apoptosis has been proposed as an additional mechanism for CD4+ T cell loss in HIV infection (Ameisen and Capron, 1991; Terai et al., 1991; Laurent-Crawford et al., 1991). Recent reports indicate that apoptosis occurs to a greater extent in HIV-infected individuals than in non-infected persons, both in the peripheral blood and lymph nodes (Finkel et al., 1995; Pantaleo and Fauci, 1995b; Muro-Cacho et al., 1995).

It has also been observed that HIV infects precursors of CD4$^+$ T cells in the bone marrow and thymus and damages the microenvironment of these organs necessary for the optimal sustenance and maturation of progenitor cells (Schnittman et al., 1990b; Stanley et al., 1992). These findings may help explain the lack of regeneration of the CD4+ T cell pool in patients with AIDS (Fauci, 1993a).

Recent studies have demonstrated a substantial viral burden and active viral replication in both the peripheral blood and lymphoid tissues even early in HIV infection (Fox et al., 1989; Coombs et al., 1989; Ho et al., 1989; Michael et al., 1992; Bagnarelli et al., 1992; Pantaleo et al., 1993b; Embretson et al., 1993; Piatak et al., 1993). One group has reported that 25 percent of CD4$^+$ T cells in the lymph nodes of HIV-infected individuals harbor HIV DNA early in the course of disease (Embretson et al., 1993). Other data suggest that HIV infection is sustained by a dynamic process involving continuous rounds of new viral infection and the destruction and replacement of over 1 billion CD4$^+$ T cells per day (Wei et al., 1995; Ho et al., 1995).

Concerning the prognosis of progression of the disease in HIV-infected patients, a first current method consists of evaluating the increase in the number of HIV viruses which are present in a whole blood sample collected from a patient, for example by performing conventional immunoassays with antibodies specifically directed against HIV proteins, and more specifically against the HIV capsid glycoprotein gp120.

A second current method for the prognosis of progression of AIDS in a patient consists of measuring the number of copies of the HIV genome which is found in a whole blood sample collected from that patient, for example through performing a quantitative PCR amplification of the nucleic acids contained in said sample, using one or several nucleic acid primer(s) that specifically hybridise with the HIV genomic RNA.

These two methods above are useful, since numerous studies have shown that people with high levels of HIV in their blood stream are more likely to develop new AIDS-related symptom or die than individuals with lower levels of the virus.

A third current method for the prognosis of progression of AIDS in a patient consists of measuring the absolute $CD4^+$ T-cell levels in whole blood samples from infected patients ($HIV^+$ patients), for example by carrying out flow cytometry from a blood sample of that patient, using a labelled antibody directed against the CD4 antigen.

All of these prognosis methods above can reproducibly be used but also have their respective technical limits, in relation with, for example, their biological significance as regards the evolution of the disease.

The use of antibodies for evaluating the number of HIV viral particles present in a biological sample form a patient comprise drawbacks due to the specificity of the antibodies which are used, since it is well known that the HIV structural proteins produced by distinct HIV virus isolates significantly differ in their antigenic properties and that false negative results may thus be generated.

The measure of the number of copies of the HIV genome in a biological sample from a patient is indeed indicative that the provirus which has integrated within the infected individual's cell genome has entered into active replication cycles and that the disease is in active progression. However, this technique does not simultaneously reflect the patient's immune response against the virus progression.

The measure of the $CD4^+$ T-cell levels in a patient is also indicative of the disease progression, since the pathogenesis of acquired immunodeficiency syndrome (AIDS) is largely attributable to the decrease in T-lymphocytes bearing the CD4 receptor ($CD4^+$). Progressive depletion of $CD4^+$ T-lymphocytes is associated with an increase of clinical complications. Because of this association, the measurement of $CD4^+$ T-cell levels is used to establish decision points for monitoring the relevance of treatments against AIDS. $CD4^+$ T-lymphocyte levels are also used as prognostic indicators in patients with human immunodeficiency virus (HIV) disease.

However, the measure of the $CD4^+$ T-cell levels in a patient does not directly reflect the immunological status of the patient, excepted as regards the resulting immunodeficiency. Notably the measure of the $CD4^+$ T-cell levels does not account for the status of the possible biological effectors that cause or mediate the observed $CD4^+$ depletion, and thus of the possible biological effectors that cause this observed patient's immunodeficiency.

Indeed, it may also be mentioned that a forecast of the progression of AIDS, in a given patient infected with HIV, can also be carried out through the detection of mutations occurring in the amino acid sequence of known co-receptors for HIV that are expressed by the patient's cells, especially $CD4^+$ cells, such as the CCR5 co-receptor, since it has been observed that HIV-infected people bearing a specific mutation in one of their two copies encoding the CCR5 co-receptor may have a slower disease course that people with two normal copies of this gene.

However, there remains a need in the art for additional methods that will allow the one skilled in the art to determine the status of progression of AIDS in patients who have been infected with a HIV virus so as to enable a more precise prognosis of the evolution of the disease, including the occurrence of, or the evolution of, the numerous well known AIDS-related diseases, and also to enable a more precise monitoring of the therapeutical treatment which may be the more beneficial to the HIV-infected patient, once taken into account the progression status of the AIDS disease. For example, there is a need in the art for novel biological markers which are indicative of the progression of AIDS, which should preferably be of biological relevance as regards the biology of the HIV infection, such as, for example, novel biological markers of relevance as regards the immunological status of the patient tested.

Indeed, these novel biological markers might be used in combination with one or several already known markers such as those cited above.

Further, there is still a need in the art for novel therapeutically useful compounds for preventing individuals from the occurrence of AIDS upon infection with a HIV virus or, more generally, for treating patients infected with a HIV virus. Particularly, in the definition of novel anti-HIV multi-therapies or HAART ("Highly Active Anti-retroviral Therapy"), there is a need to include novel pharmaceutically active compounds that will specifically be directed against other target molecules than the HIV protease and the HIV retrotranscriptase and which will act on targets involved in distinct stages of the disease. Notably, there is a need in the art for novel compounds of pharmaceutical interest that are biologically active in HIV-infected patients wherein HIV has begun to actively replicate, especially in HIV-infected patient which are close to undergo a decrease in the number of their $CD4^+$ T-cells and who are thus susceptible to immunodeficiency, as well as in HIV-infected patients for whom the depletion of their $CD4^+$ T-cells has already begun.

SUMMARY OF THE INVENTION

The invention is firstly directed to a method for the in vitro assessment of the progression status of the infection of an individual with an HIV virus, wherein said method comprises the steps of:
(a) incubating said biological sample with a ligand compound which specifically binds onto the NKp44L protein of SEQ ID No1, or onto the extracellular domain portion thereof; and
(b) measuring the amount of said ligand compound which is bound to the $CD4^+$ T cells, whereby said measured amount of said bound ligand compound is indicative of the progression status of the viral infection.

It also relates to kits which are specifically designed for implementing the method above.

The invention also deals with in vitro methods for the screening of compounds that are therapeutically active in HIV-infected patients.

Particularly, the invention is directed to a method for the in vitro screening of compounds for preventing or treating a disease linked with the infection of an individual with an HIV virus, wherein said method comprises the steps of:
(a) bringing into contact a first cell population consisting of human activated NK cells and a second cell population consisting of human $CD4^+$ T-cells expressing the NKp44L protein in the presence of a candidate therapeutical compound to be tested;
(b) measuring the cytolysis of the $CD4^+$ T-cells by the activated NK cells;
(c) comparing the cytolysis value obtained at step (b) with the cytolysis value obtained when step (a) is performed in the absence of the candidate compound;
(d) selecting the candidate compounds that inhibit or block the NK-mediated cytolysis of the $CD4^+$ T-cells.

It also relates to a pharmaceutical composition for preventing or treating a disease linked to the infection of an individual with a virus of the HIV family, which comprises an effective amount of a ligand compound which is selected form the group consisting of (i) a ligand compound which specifically binds to the NKp44L protein of SEQ ID No1, or to the extracellular domain portion thereof and (ii) a ligand compound which specifically binds to the NKp44 protein of SEQ ID No2, or to the extracellular domain portion thereof, in combination with at least one physiologically acceptable excipient.

It also relates to a pharmaceutical composition for preventing or treating a disease linked to the infection of an individual with a virus of the HIV family, which comprises an effective amount of an antisense polynucleotide that specifically hybridises with the mRNA molecules encoding the NKp44L protein of SEQ ID No1, in combination with at least one physiologically acceptable excipient.

It is also directed to methods for treating HIV-infected patients that make use of the therapeutically active compounds and of the pharmaceutical compositions that are further described in the present specification.

In another aspect, the present invention relates to a polypeptide comprising the following amino acid sequence: $X_1X_2X_3X_4X_5X_6SWSNKSX_{13}X_{14}X_{15}X_{16}X_{17}$ (I) (SEQ ID NO: 5),
wherein $X_1$, $X_2$, $X_3$, $X_5$, $X_6$, $X_{13}$, $X_{15}$, $X_{16}$ and $X_{17}$ mean, independently one from each other, any amino acid residue, $X_4$ means any amino acid residue except A and W, and wherein $X_{14}$ means any amino acid residue except E and S.

The invention also deals with in vitro methods for the screening of compounds for preventing or treating a disease linked with the infection of an individual with an HIV virus, wherein said method comprises the steps of:
(i) incubating a candidate compound to be tested with a polypeptide as described above,
(ii) assaying for the binding of the candidate compound to be tested with a polypeptide as described above.

It also relates to a pharmaceutical composition for preventing or treating a disease linked to the infection of an individual with a virus of the HIV family, which comprises an effective amount of a ligand compound which specifically binds to the polypeptide of formula (I) in combination with at least one physiologically acceptable excipient.

1A) Specific expression of NKp44L on CD4$^+$ T cells in HIV-1 infected patients. Comparison between uninfected (Control, open symbols) and HIV-infected (closed symbols) groups. The horizontal lines mark the mean value. Abscissa: phenotype of the blood cells tested. Ordinates: Percent of the cells tested that are positive for the NKp44L marker.

1B) Inverse correlation of NKp44L expression in CD4$^+$ T cells with peripheral blood CD4 cell count in HIV-infected patients. The correlation (r) and this statistical significance (P) obtained using the Sperman's non-parametric rank correlation test is shown. Abscissa: number of CD4$^+$ T-cells per mm$^3$ of patient whole blood sample. Ordinate: Percent of the CD4$^+$ cells tested that are positive for the NKp44L marker.

1C) Correlation between NKp44L expression in CD4$^+$ T cells and viral load. The correlation (r) and this statistical significance (P) obtained using the Sperman's non-parametric rank correlation test is shown. Abscissa: value of viral load, as expressed by the number of HIV genome copies per ml of the patient's whole blood sample. Ordinate Percent of the CD4$^+$ cells tested that are positive for the NKp44L marker.

1D) Over-expression of NKp44L in CD4$^+$ T cells from HIV-infected individuals after PHA activation. Comparison between 5 uninfected (Control, open symbols) and 5 HIV-infected (closed symbols) patients. NA: Non-activated cells; PHA: PHA-activated cells. Abscissa: NA=Non-Activated cells PHA=PHA-activated cells in respectively control and HIV-infected individuals. Ordinate: Percent of the CD4$^+$ cells tested that are positive for the NKp44L marker.

Figure 2:
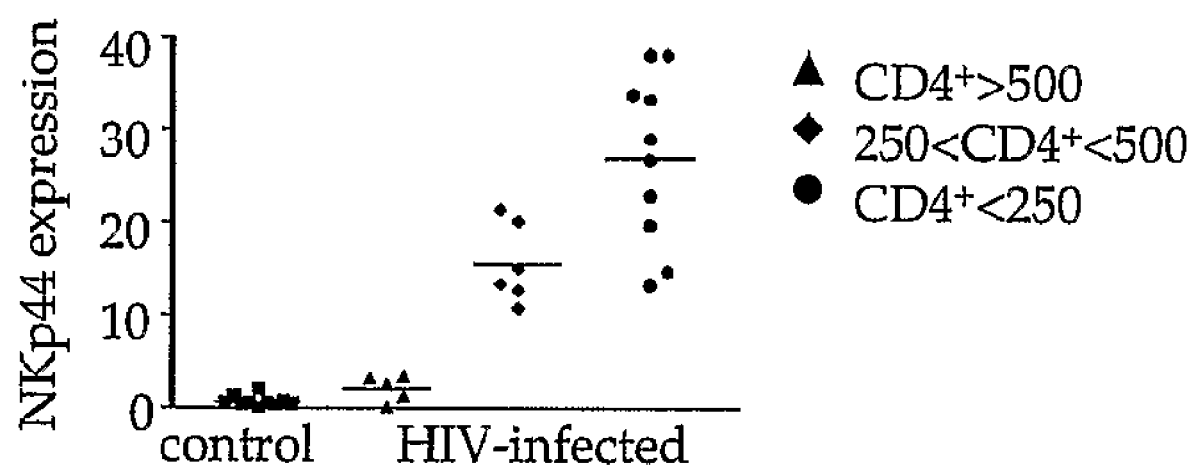

FIG. 2. Expression of NKp44 on CD3$^-$CD56$^+$ NK cells from HIV-infected patients.

The proportion of NK cells which expressed NKp44 was significantly higher in the HIV-infected individuals with less than 500 CD4$^+$ cells/mm$^3$ than the uninfected cells (control).

Figure 3:
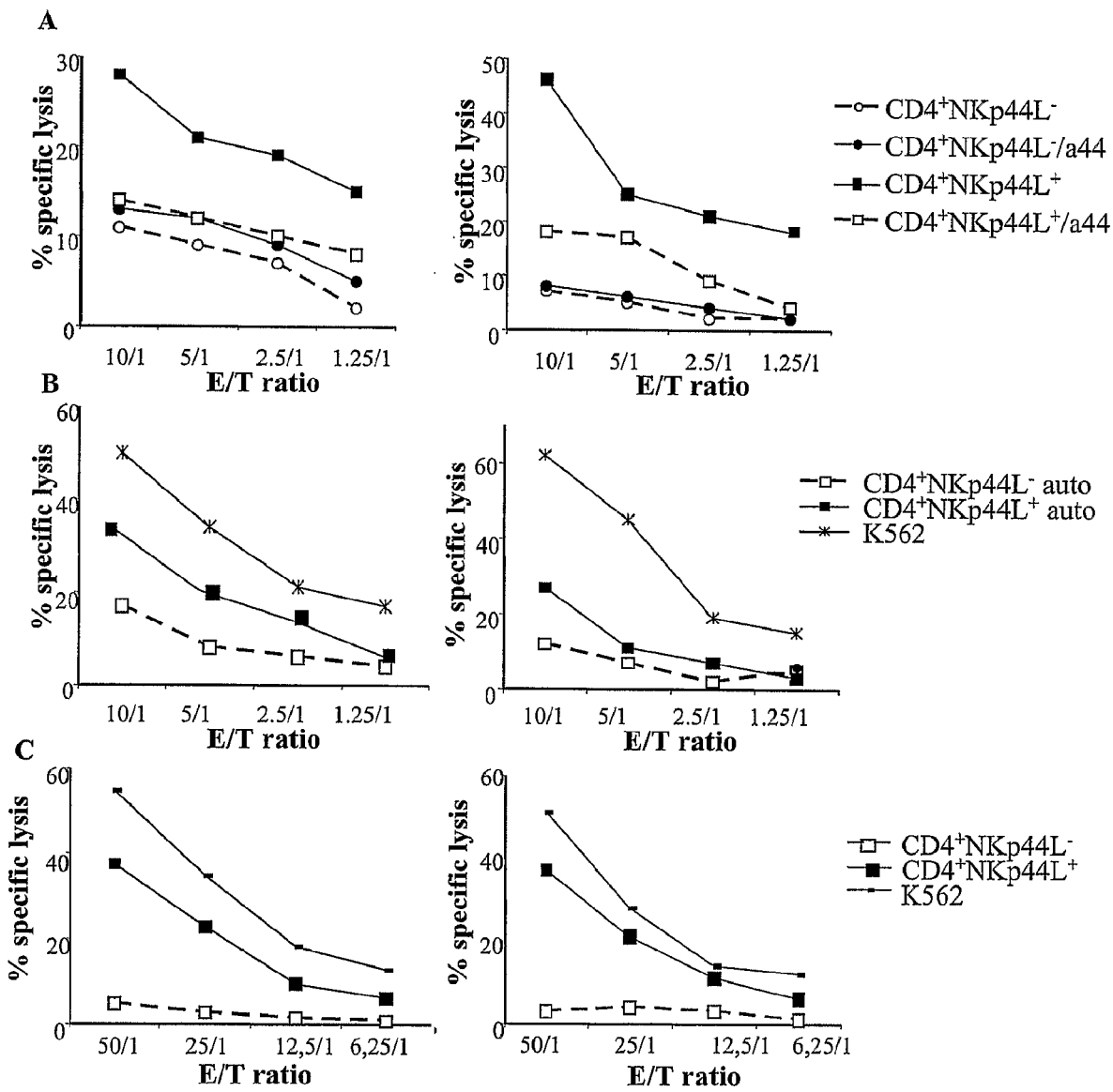

FIG. 3. Higher NK-lysis sensitivity of CD4$^+$ T cells expressing NKp44L from HIV-infected patients.

3A) NK92 NK line was analyzed for cytotoxic activity against two purified CD4$^+$ T cells expressing (circle) or not (square) NKp44L. Cytotoxic activity was partially blocked after treatment with anti-NKp44L mAb (a44).

3B) Cytotoxic activity of two IL-2-activated autologous (auto) NK primary cells against purified CD4$^+$ T cells expressing (circle) or not (square) NKp44L, and K562 (star), as positive control for cytotoxic activity.

3C) Cytotoxic activity of unactivated autologous (auto) NK primary cells against two purified CD4$^+$ T cells expressing (circle) or not (square) NKp44L, and K562 (star), as positive control for cytotoxic activity.

In FIGS. 3A, 3B and 3C, left and right panels represented two independent assays and show the reproducibility of the results.

Figure 4:
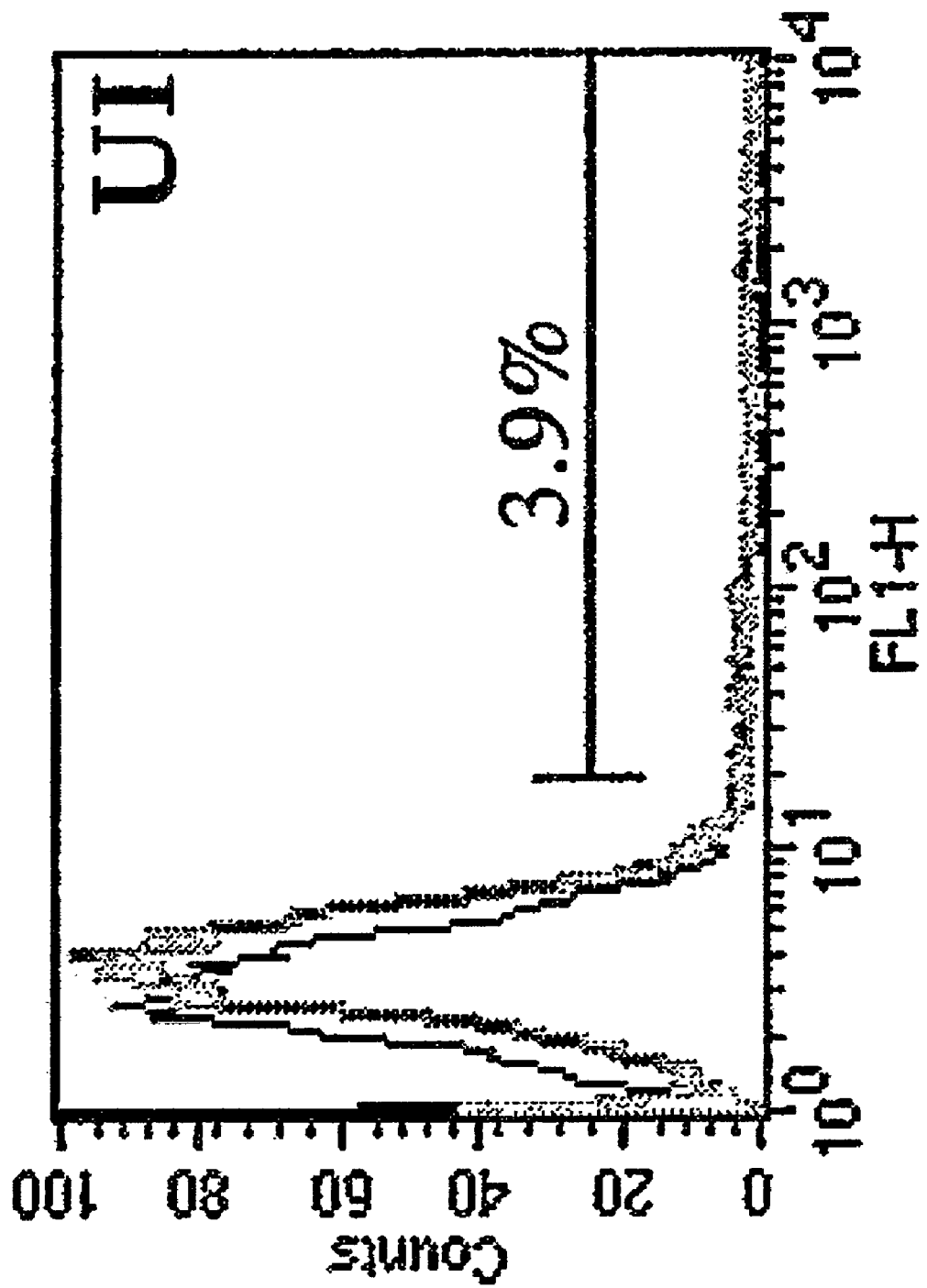
Figure 4:
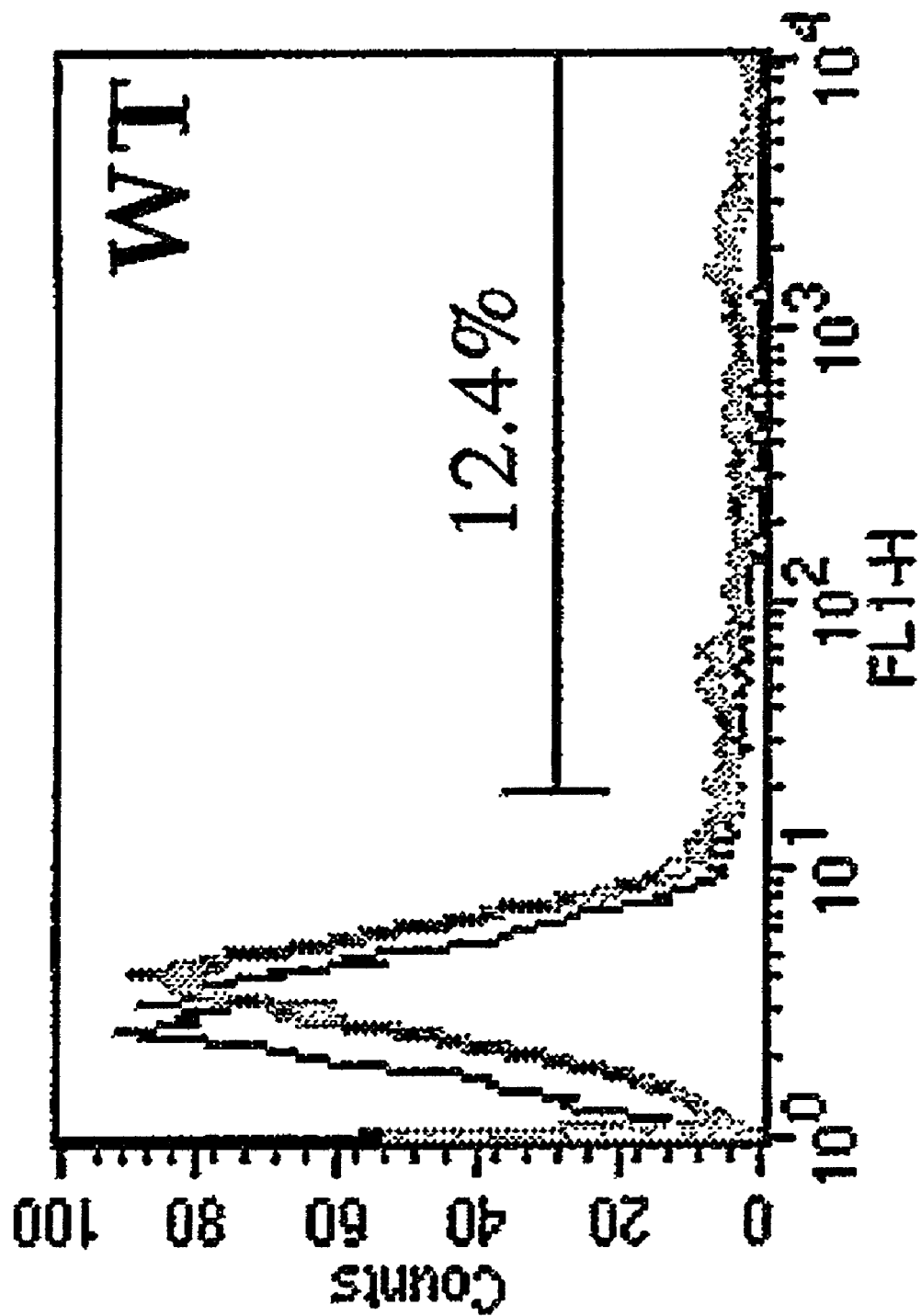
Figure 4:
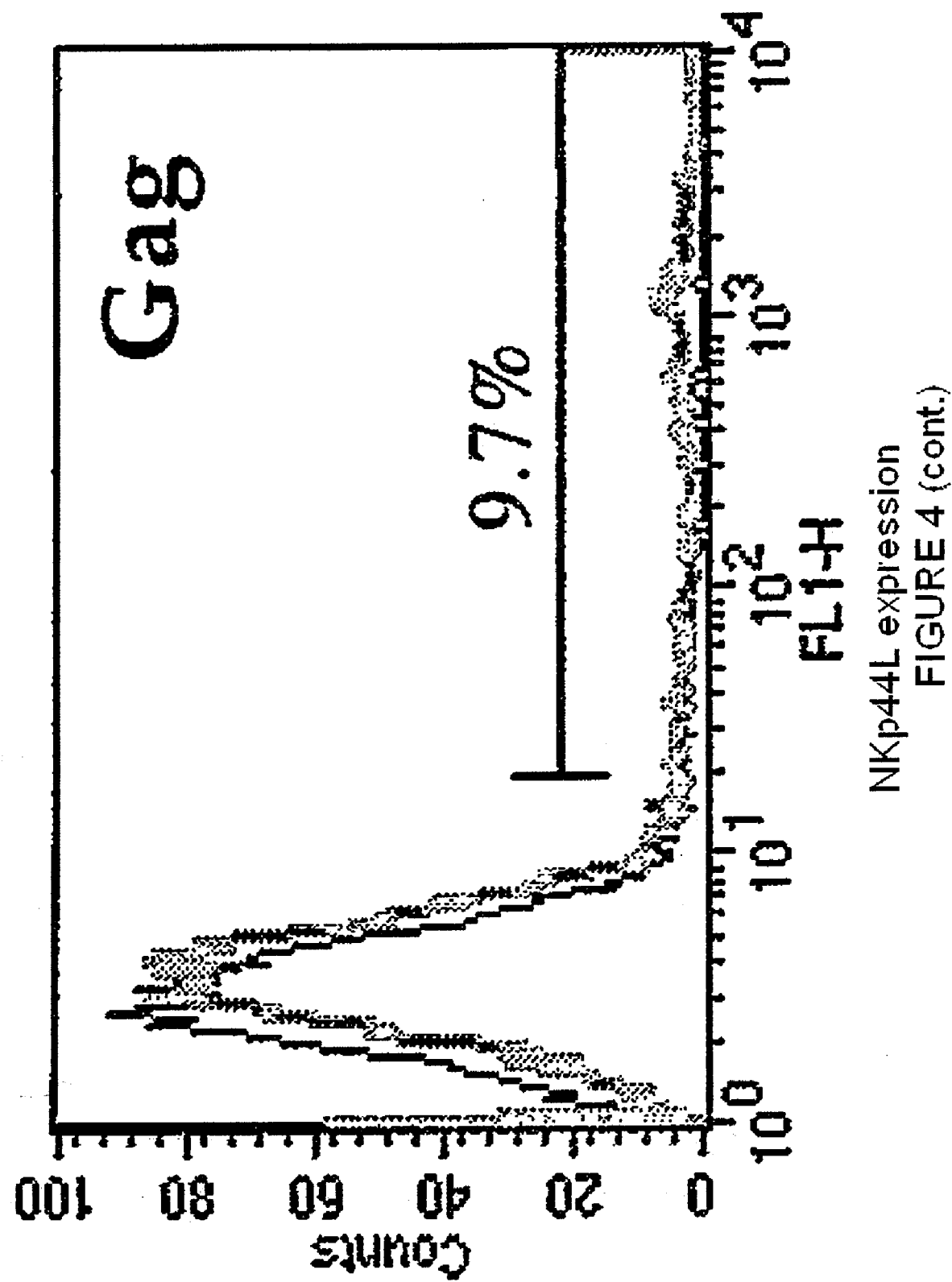
Figure 4:
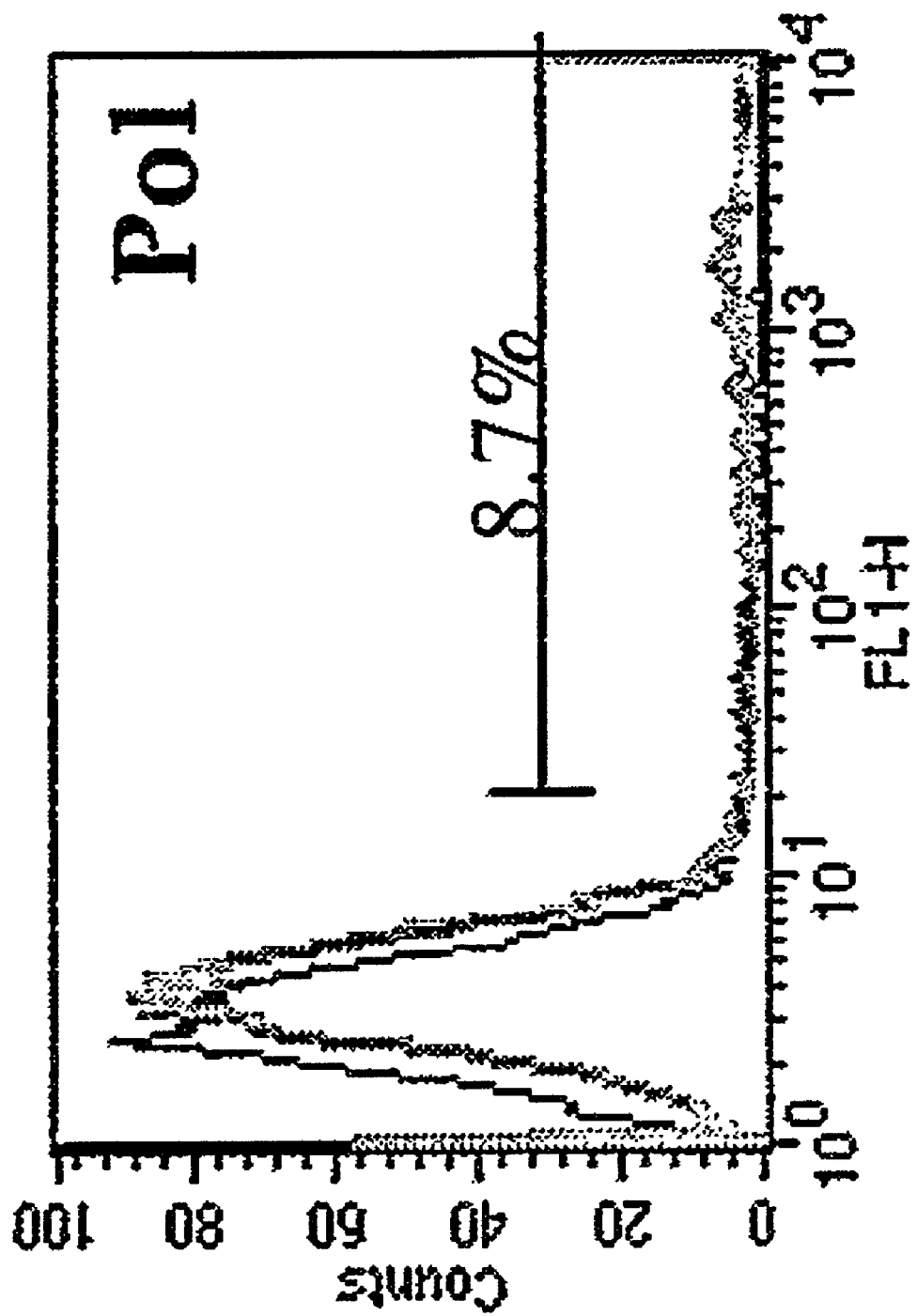
Figure 4:
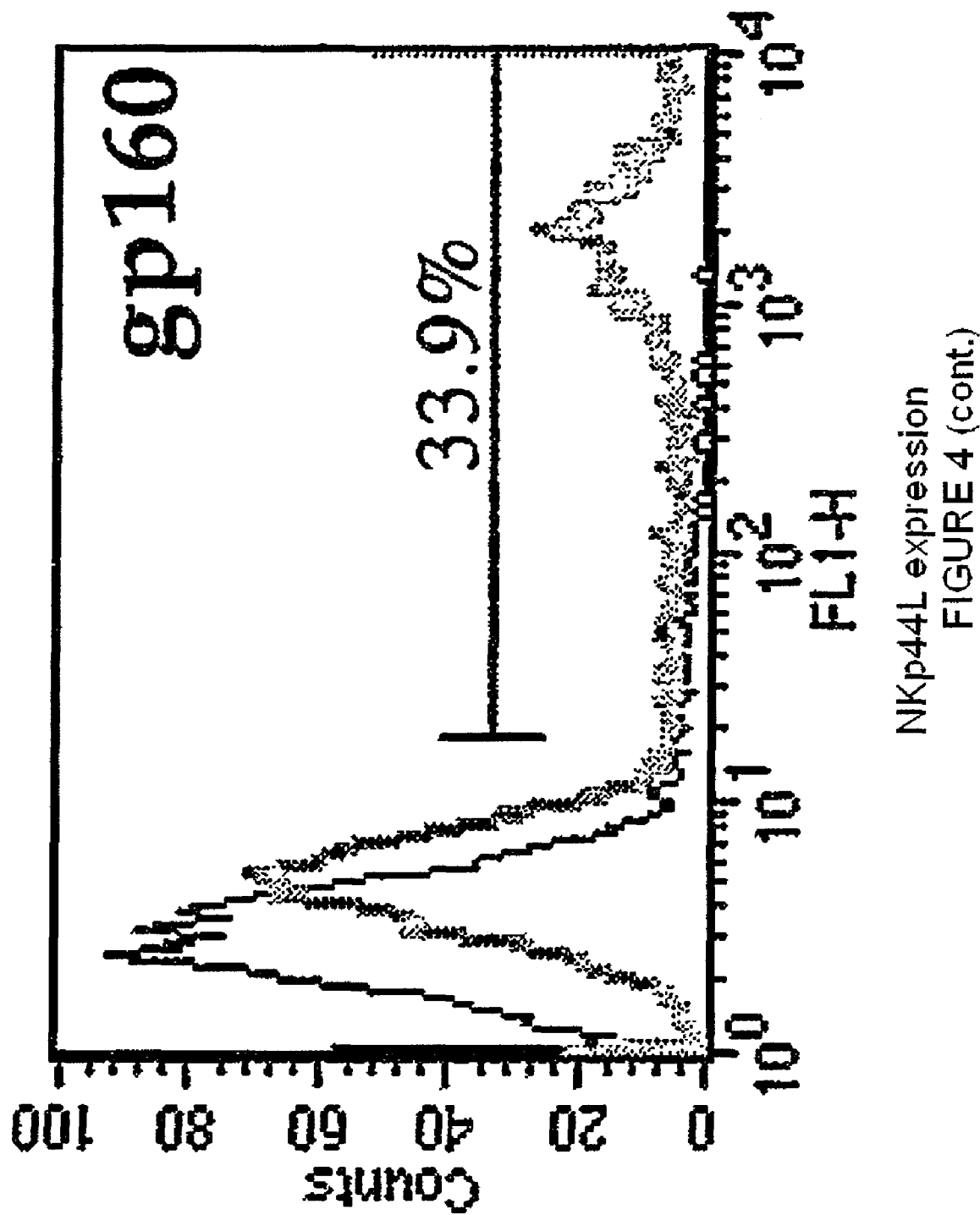
Figure 4:
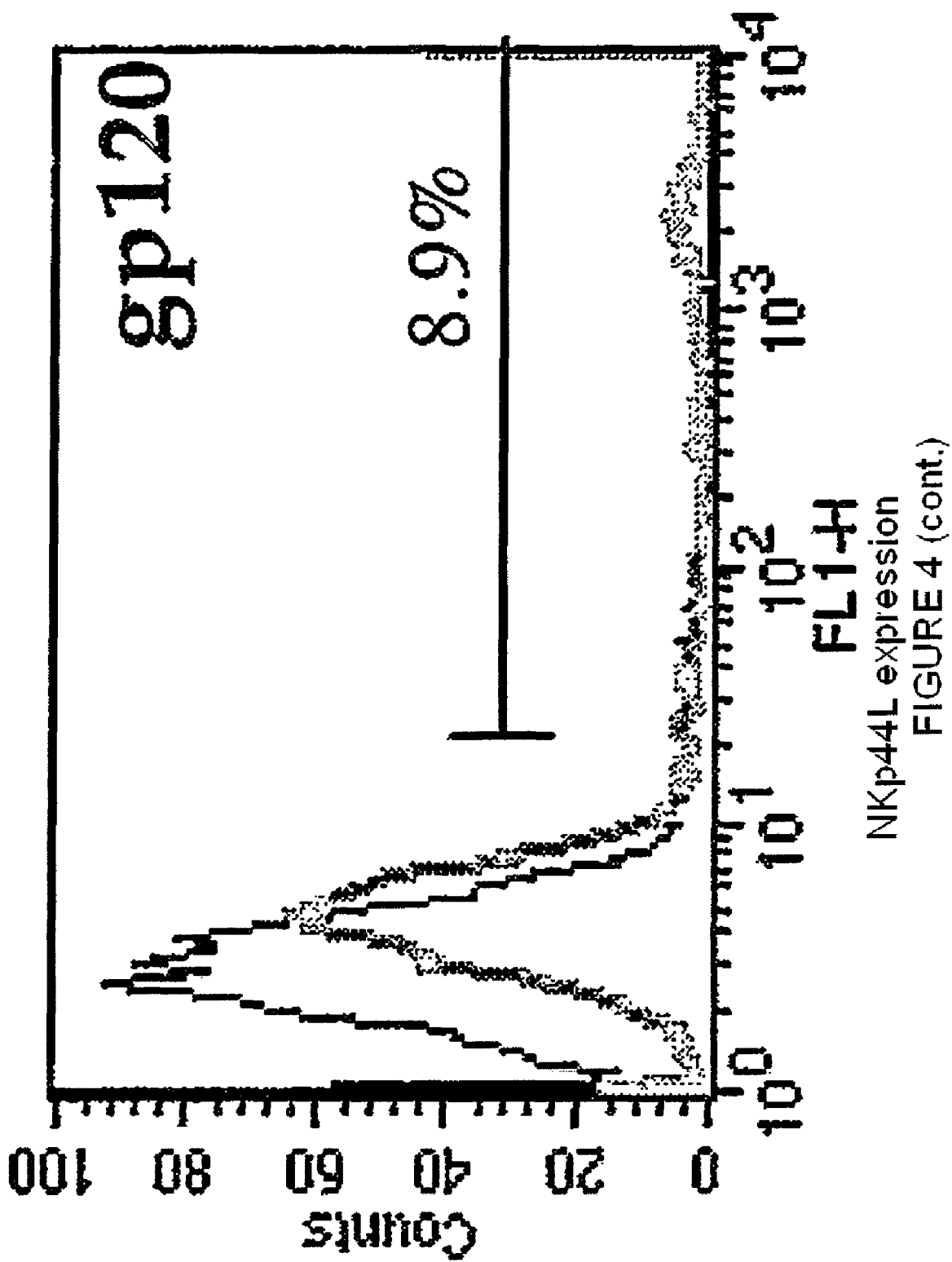
Figure 4:
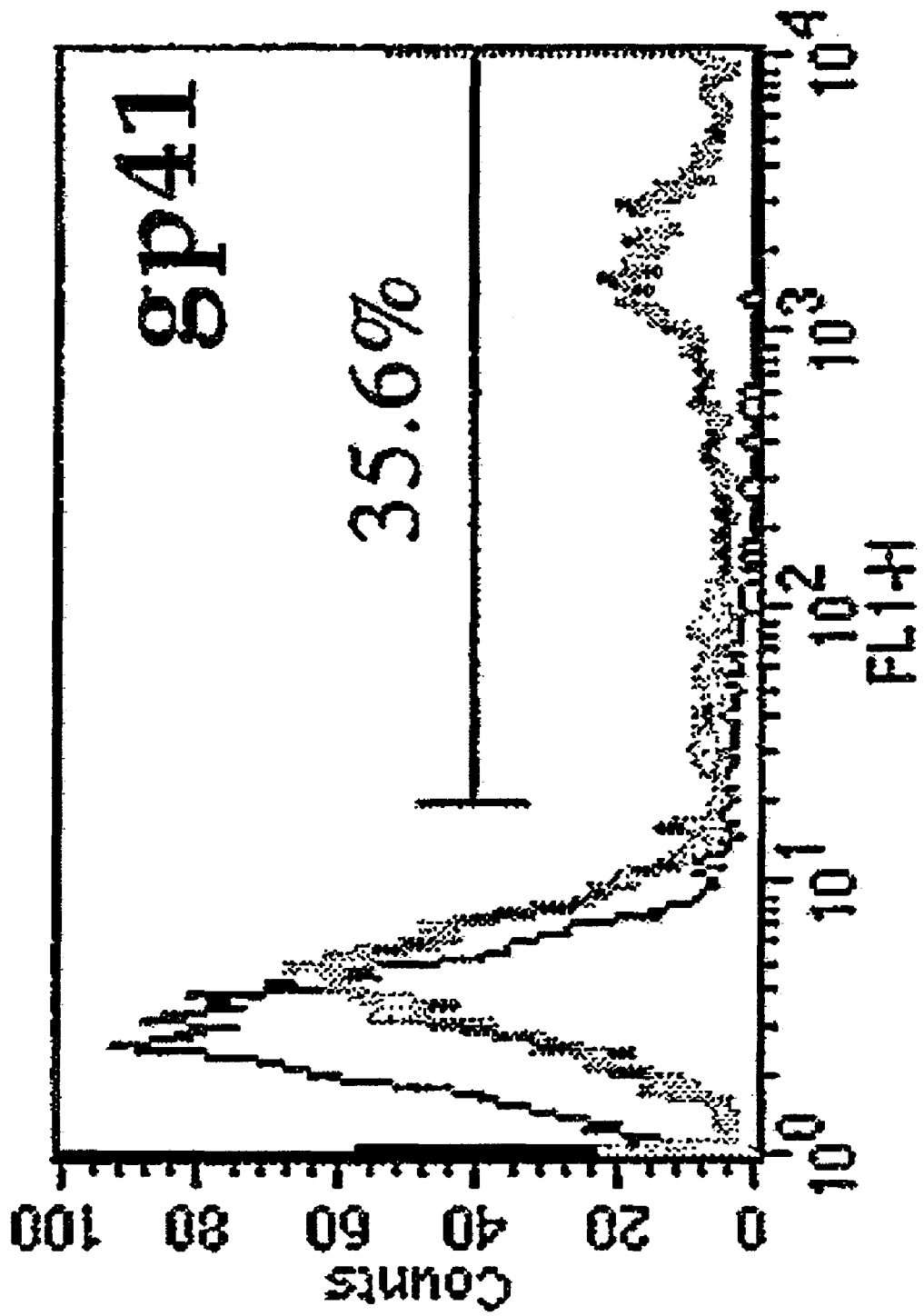
Figure 4:
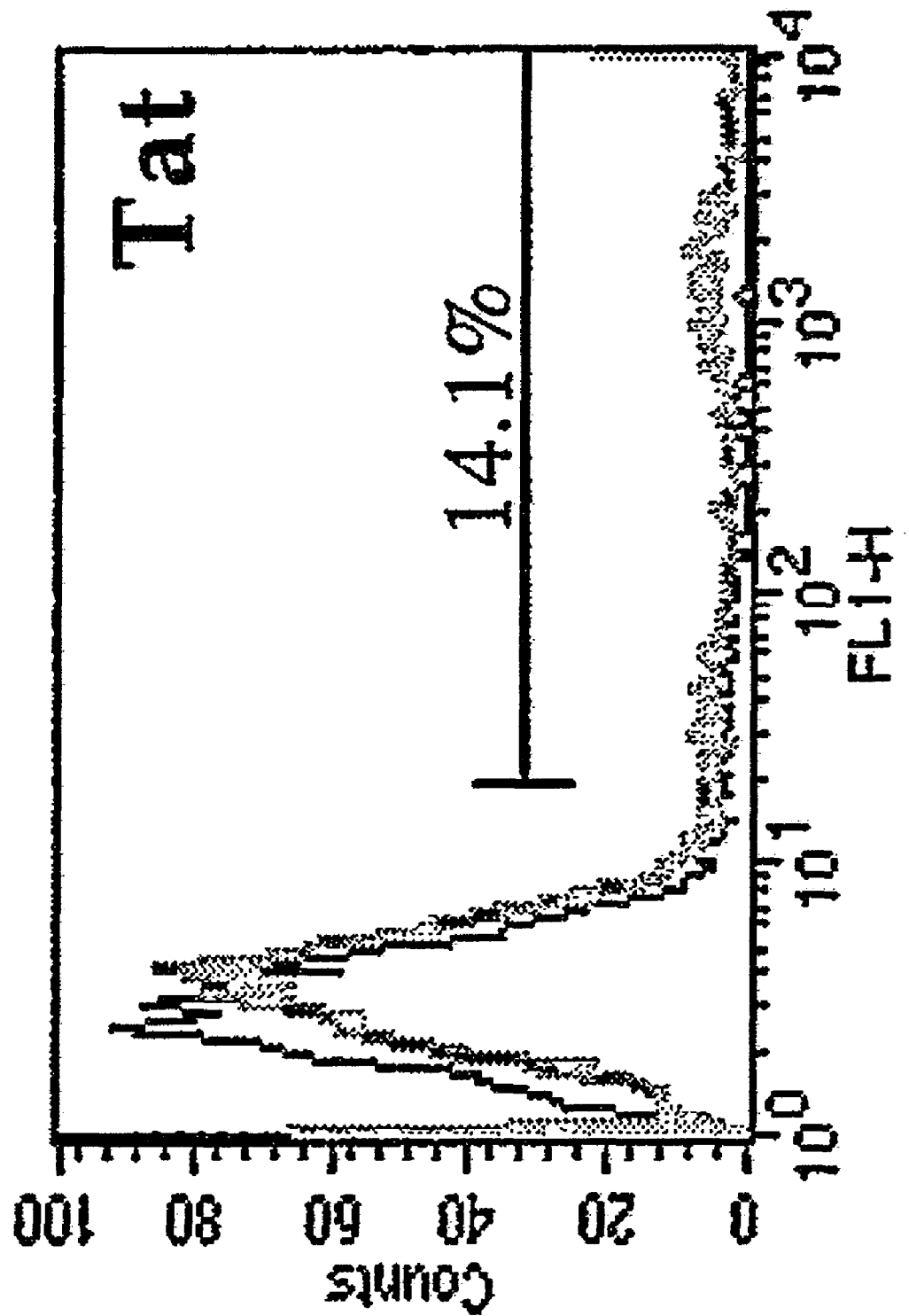
Figure 4:
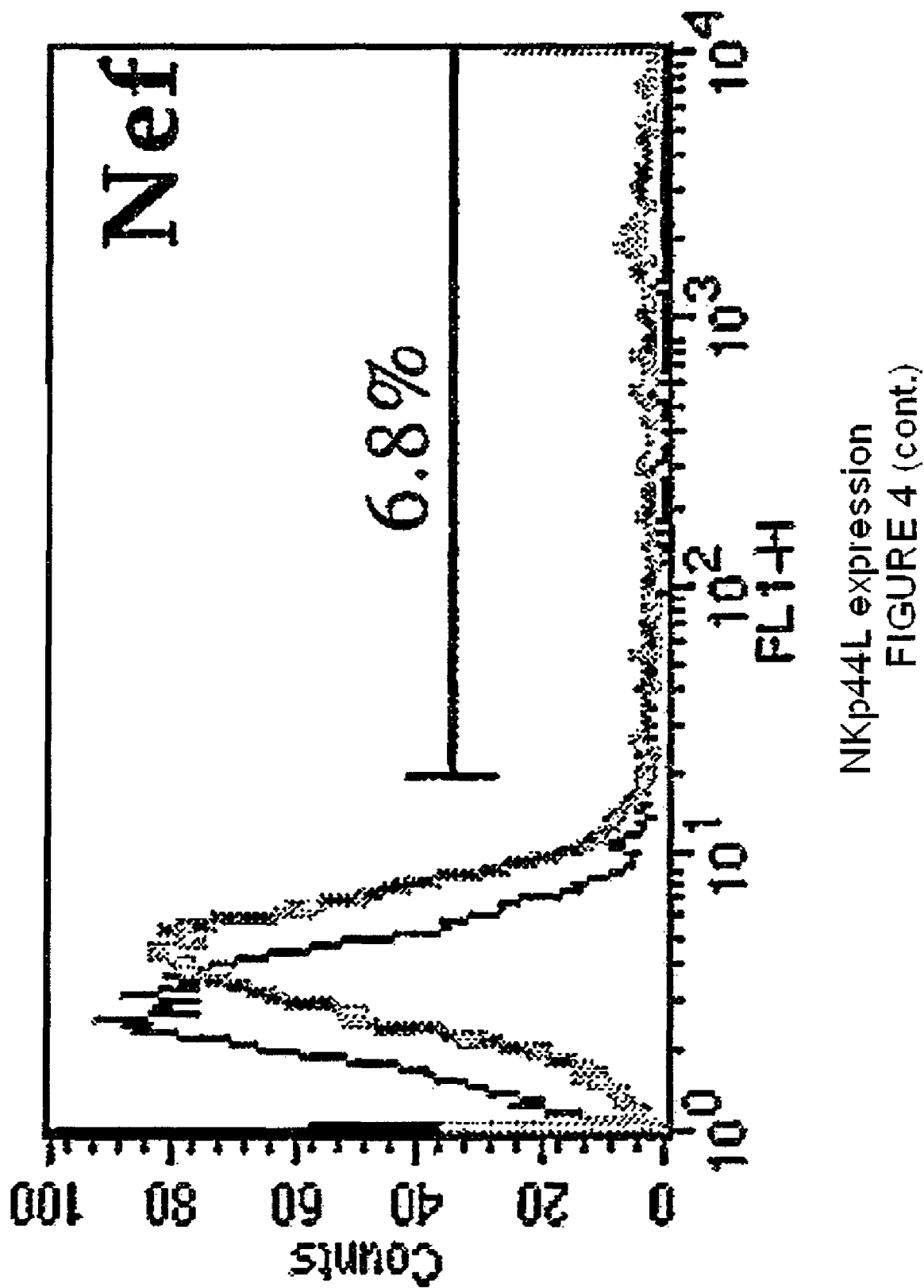

FIG. 4. Over-expression of NKp44L after treatment of purified CD4+ T cells with vaccinia virus expressing several HIV proteins.

Purified CD4+ T cells were infected with 20 pfu/cell of several recombinant vaccinia virus expressing HIV protein. Two days later, the cells were washed twice, and stained with anti-NKp44L mAb (grey thick line), or with IgM isotype control (black thin line). The cells were analyzed by flow cytometry. UI: Uninfected cells, WT: cells infected with wild type vaccinia virus. Gag, Pol, gp160, gp120, gp41, Tat, Nef: cells infected with vaccinia virus, expressing respectively Gag, Pol, gp160, gp120, gp41, Tat, or Nef. The percentage of NKp44L expression was noted for each panel.

Abscissa: NKp44L expression, Ordinates: Number of cells.

Figure 5:
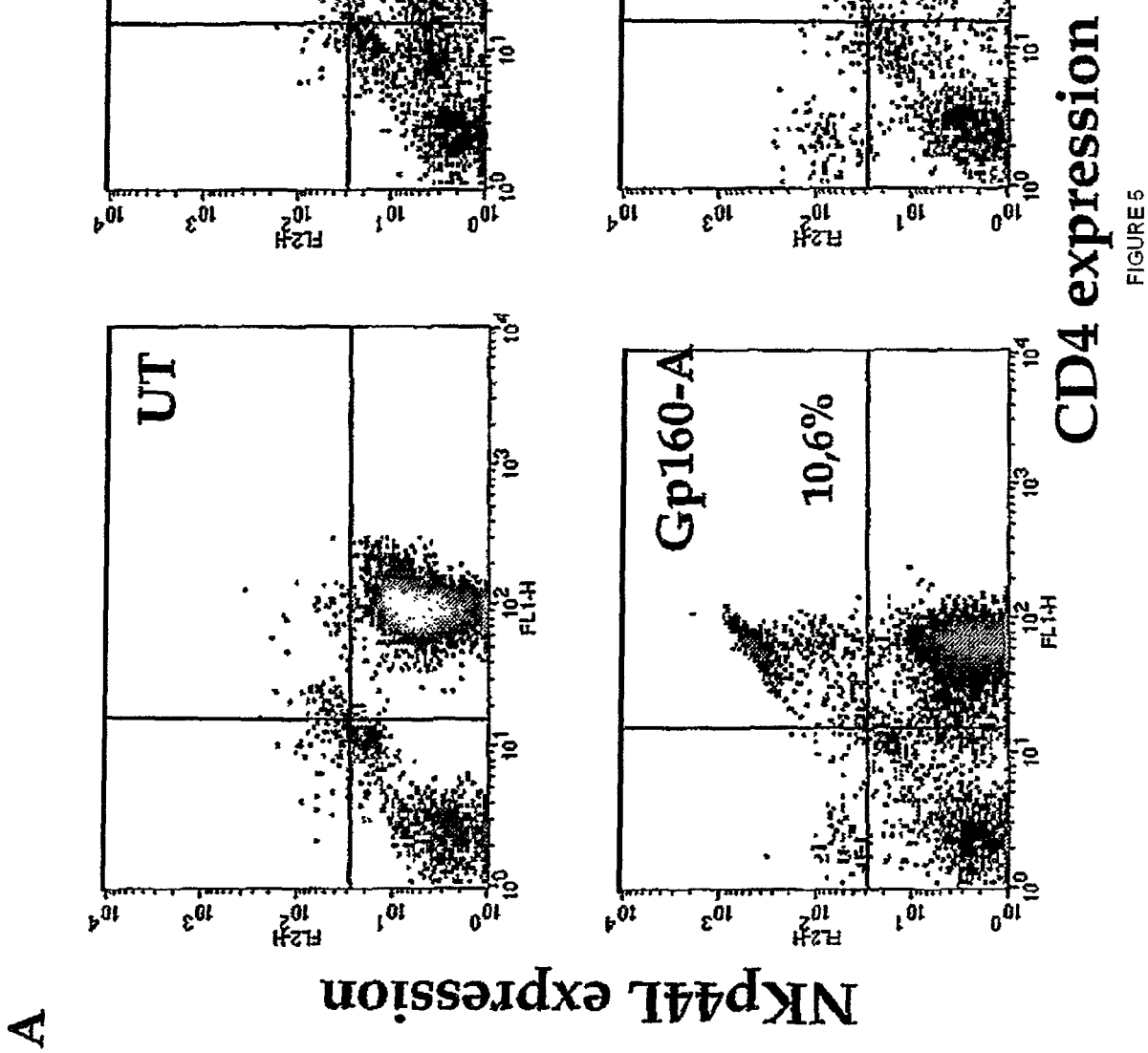
Figure 5:
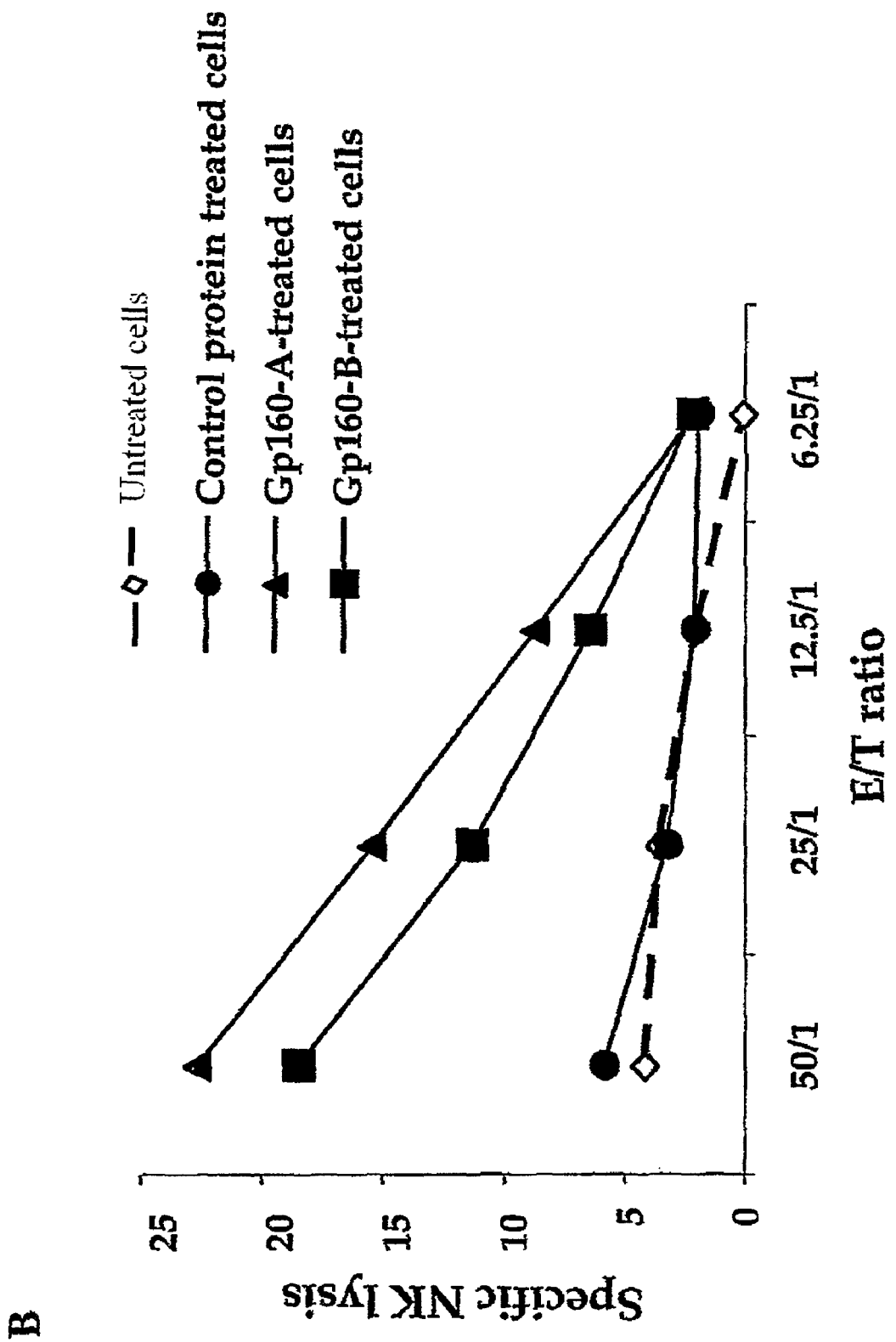

FIG. 5. Over-expression of NKp44L after treatment of purified CD4+ T cells with recombinant qp160 HIV protein.

One million of cells were incubated with 5 ug/ml of control protein (Ctl; black circle), or recombinant gp160 protein (gp160-A: black triangle); (gp160-B: black square) or without protein (UT: untreated cells) during 2 days in presence of 10 U/ml IL2.

5A) The cells were washed and stained with anti-NKp44L mAb and CD4 mAb or with isotype controls and analyzed by flow cytometry. The percentage of NKp44L expression in CD4+ T cells was noted for each panel. Abscissa: CD4 expression, Ordinates: NKp44L expression.

5B) NK-lysis sensitivity of CD4+ T cells incubated with recombinant gp160 HIV protein was analyzed for cytotoxic activity with activated autologous purified NK cells. NK lysis activity was performed at different effector/target (E/T) ratios (Abscissa). Open diamonds with dotted lines: Untreated cells; Closed bottoms: Control protein-treated cells; Closed triangles: gp160-A-treated cells; and closed squares: gp160-B-treated cells. Ordinates: Specific NK lysis (%).

Figure 6:
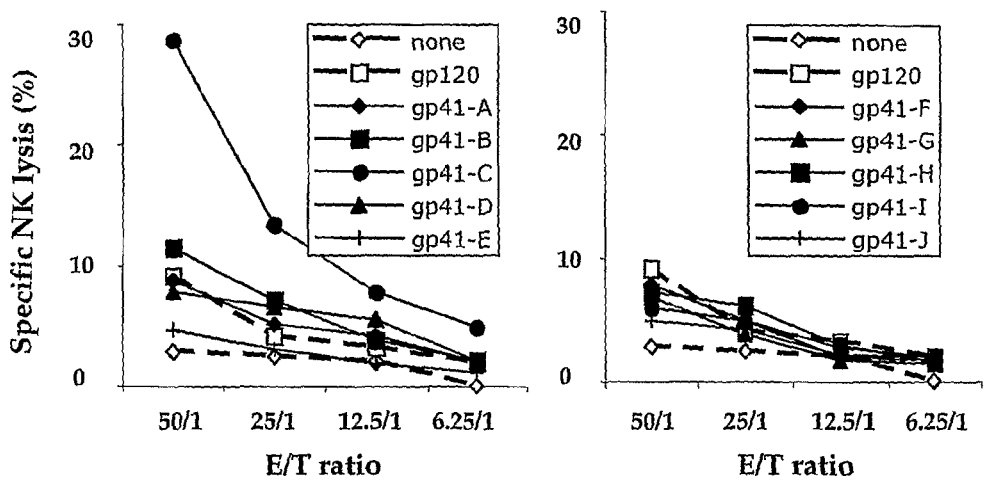
Figure 6:
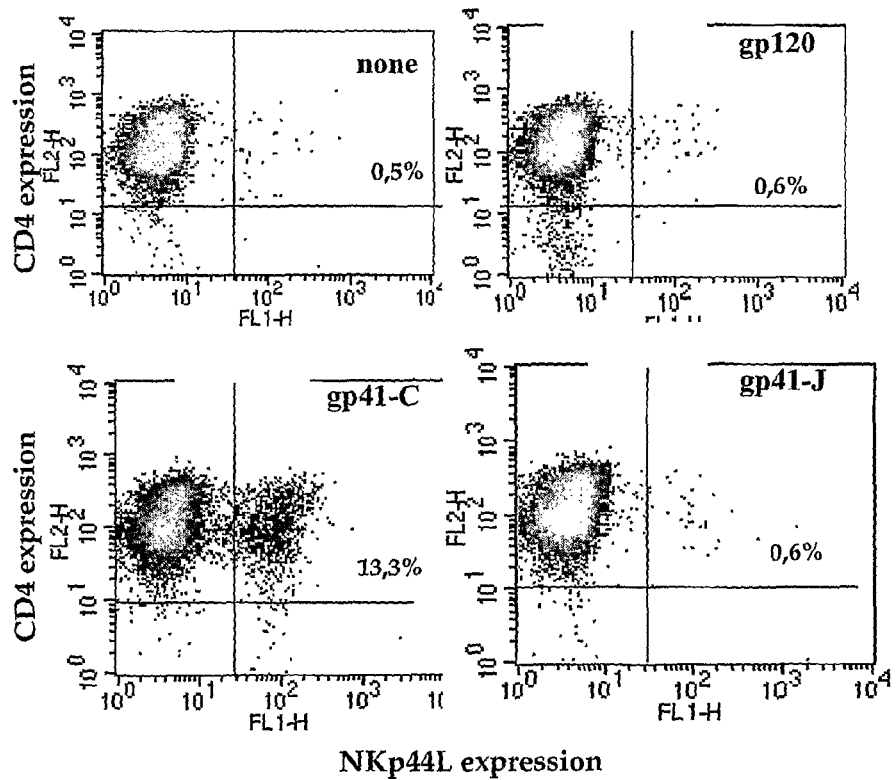

FIG. 6. One pool of peptides from the HIV qp41 protein both induced an higher sensitivity to NK lysis and an overexpression of NKp44L.

One million of purified CD4+ T cells were treated with 5 ug/ml of pools of peptides from HIV gp41 protein (noted from A to J) or from gp120 protein (gp120), as control. Each pool of peptides included 10 peptides, as described in Material and Methods section. The cells were incubated two days in presence of 10 u/ml IL2, and then washed twice.

6A) NK-lysis sensitivity of CD4+ T cells incubated with the different pools of peptides was analyzed for cytotoxic activity with activated autologous purified NK cells. NK lysis activity was performed at different effector/target (E/T) ratios (Abscissa). Ordinates: Specific NK lysis (%).

6B) The cells were stained with anti-NKp44L mAb and CD4 mAb or with isotype controls and analyzed by flow cytometry. In this panel of figures, the results were only done for the untreated cells (none) or the cells treated with polls of peptides from gp120 or from the gp41 (polls C and J). The percentage of NKp44L expression in CD4+ T cells was noted for each panel. For the other pools a low expression of NKp44L, ranged from 0.2 to 1.3%, was observed. Abscissa: NKp44L expression, Ordinates: CD4 expression.

Figure 7:
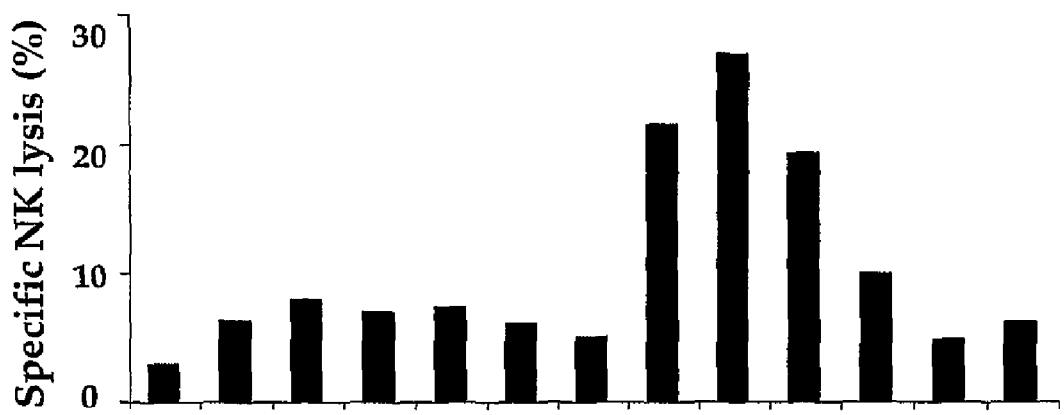
Figure 7:
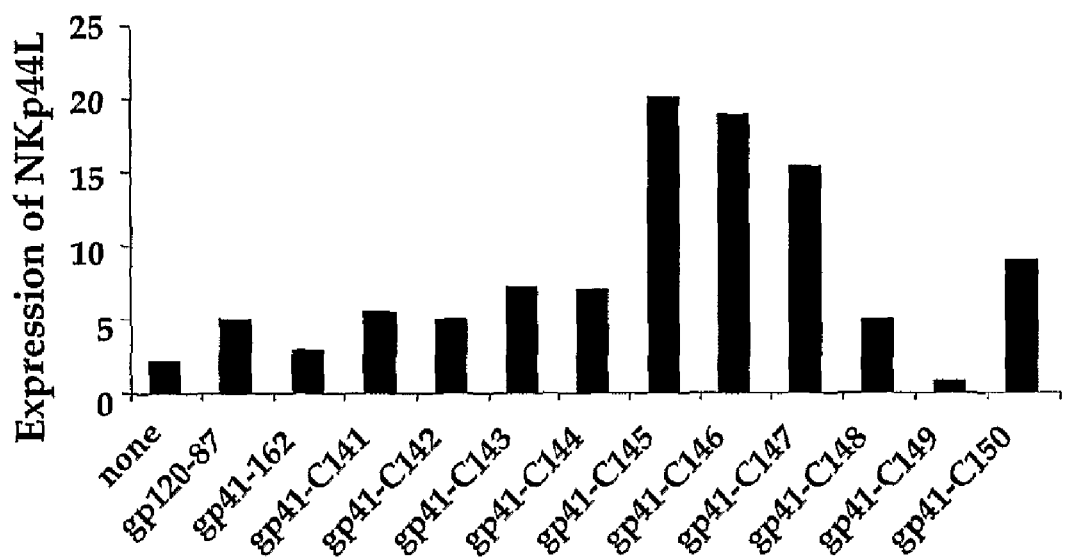

FIG. 7. Analysis of each peptide from the pool C derived from HIV qp41 protein.

One million of purified CD4+ T cells were treated with 5 ug/ml of peptides from the pool C (see FIG. 6) (noted from C141 to C150) or as controls the peptide gp41-E162 or the peptide gp120-87. The cells were incubated two days in presence of 10 u/ml IL2, and then washed twice.

7A) Killing pattern of CD4+ T cells incubated with the different peptides were tested for their sensitivity to NK. Data are shown for an E/T ratio of 40/1 with activated autologous purified NK effector cells. Ordinates: Specific NK lysis (%).

7B) The cells were stained with anti-NKp44L mAb and CD4 mAb or with isotype controls and analyzed by flow cytometry. Ordinates: Expression of NKp44L.

Figure 8:
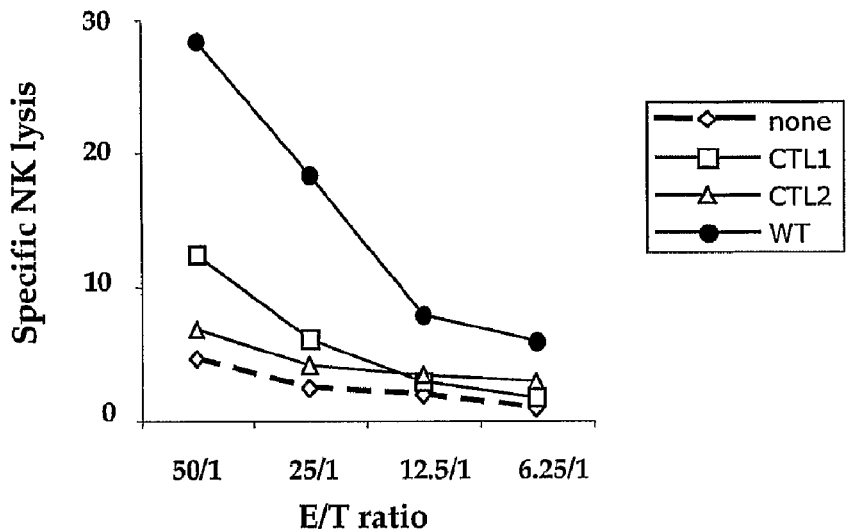
Figure 8:
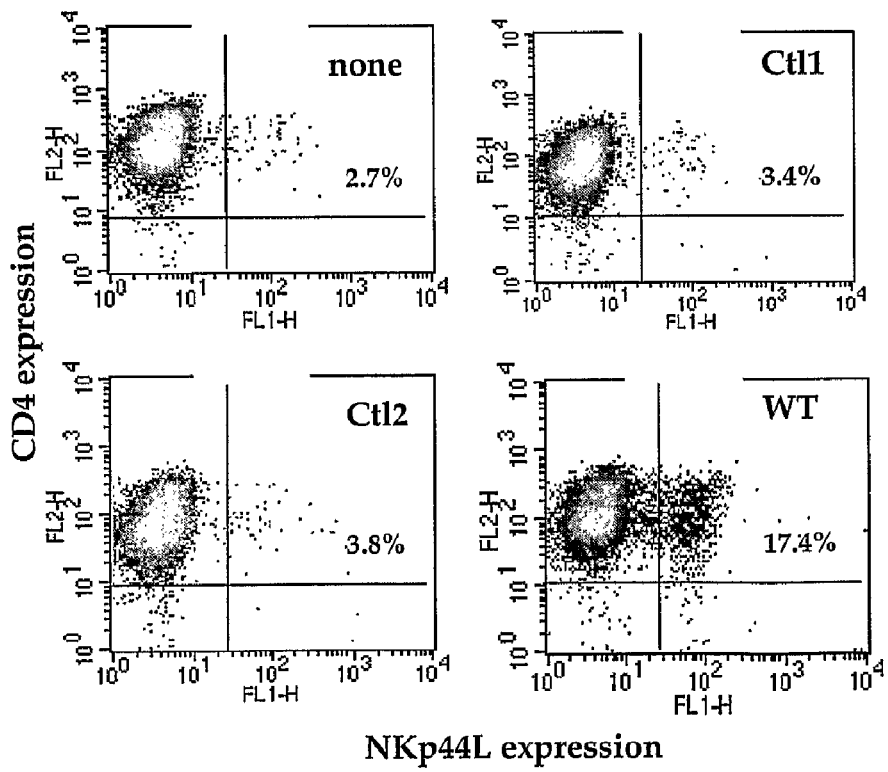

FIG. 8. Drastic role of the NH2-SWSNKS—COOH motif expressed by the gp41 HIV protein.

8A) Sequences of the peptide gp41-C147 (wild type: WT) and two different control peptides included some modification just inside the "SWSNKS" motif (control 1: Ctl1) or in all of the 15-mers sequence (control 2: Ctl2).

One million of purified CD4+ T cells were treated with 1 ug/ml of highly purified WT peptide or with the both control peptides (Ctl1 and Ctl2). The cells were incubated two days in presence of 10 u/ml IL2, and then washed twice.

8B) NK-lysis sensitivity of CD4+ T cells incubated with the different peptides was analyzed for cytotoxic activity with activated autologous purified NK cells. NK lysis activity was performed at different effector/target (E/T) ratios (Abscissa). Open diamonds with dotted lines: Untreated cells; Closed bottoms: WT peptide-treated cells; Closed squares: Ctl1-peptide-treated cells, and Closed triangles: Ctl2-peptide-treated cells. Ordinates: Specific NK lysis (%).

8C) The cells were stained with anti-NKp44L mAb and CD4 mAb or with isotype controls and analyzed by flow cytometry. The percentage of NKp44L expression in CD4+ T cells was noted for each panel. Abscissa: NKp44L expression, Ordinates: CD4 expression.

Figure 9:
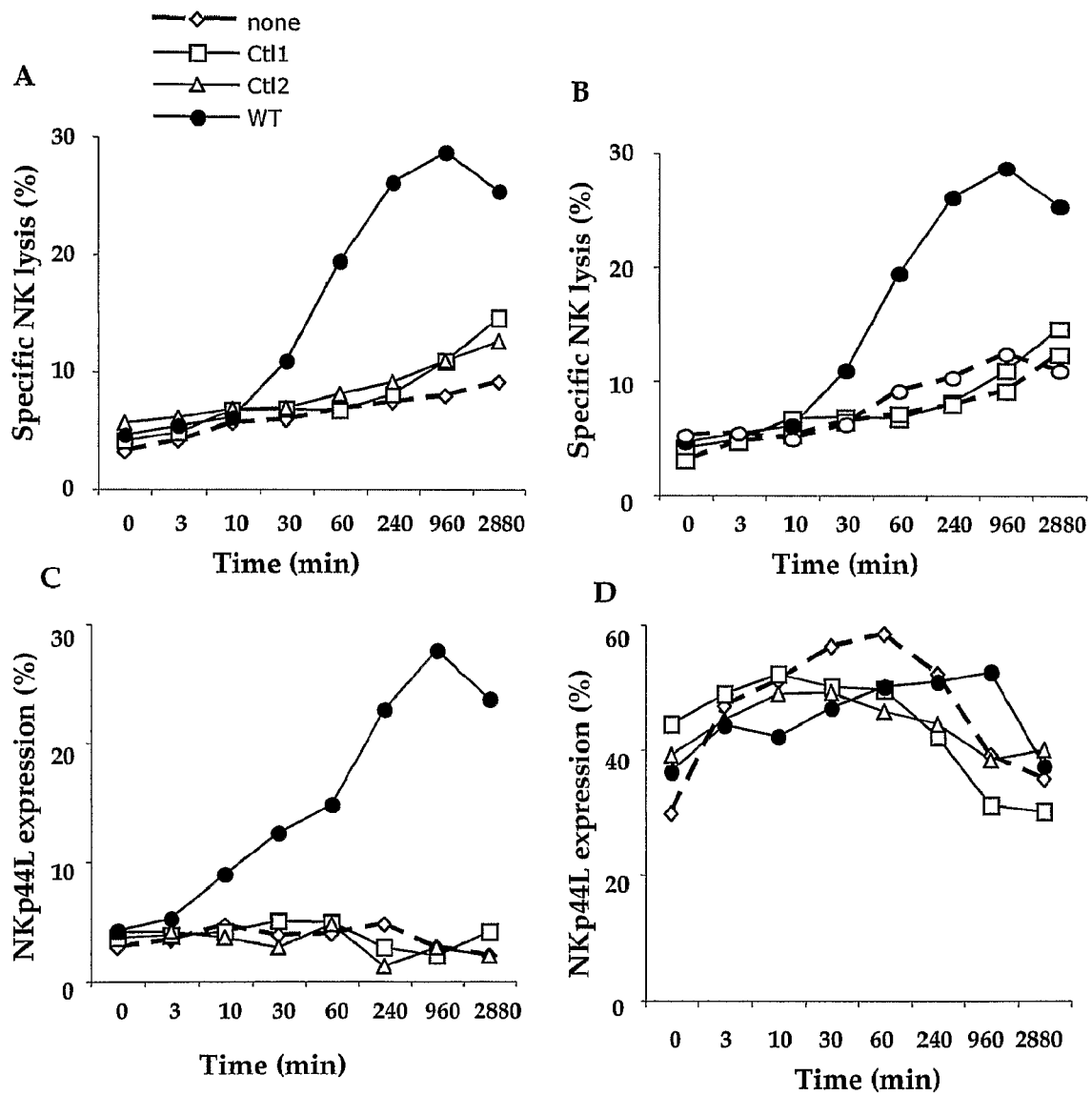

FIG. 9. Kinetics studies of NK lysis activity and NKp44L expression after addition of the "active SWSNKS" peptide.

One million of purified CD4+ T cells were treated with 1 µg/ml of highly purified wild type (WT) peptide or with the both control peptides (Ctl1 and Ctl2) during several times ranged from 0 to 2880 min. After incubation, the cells were washed twice and then analyzed for cytotoxic activity with activated autologous purified NK cells. NK lysis activity was performed at different effector/target (E/T) ratios 9A). NK cytotoxic activity was performed after pretreatment of cell with 10 ug/ml of anti-NK44L mAb (B). Flow cytometry analysis revealed the cell surface expression of NKp44L (A), and for the intra-cellular expression of NKp44L (B). Open diamonds with dotted lines: Untreated cells; Closed bottoms: WT peptide-treated cells; Closed squares: Ctl1-peptide-treated cells, and Closed triangles: Ctl2-peptide-treated cells; Open bottoms with dotted line: WT-peptide-treatment cells after pretreatment with anti-NKp44L mAb and Open squares with dotted line: Ctl1-peptide-treated cells after pretreatment with anti-Nkp44L mAb.

Figure 10:
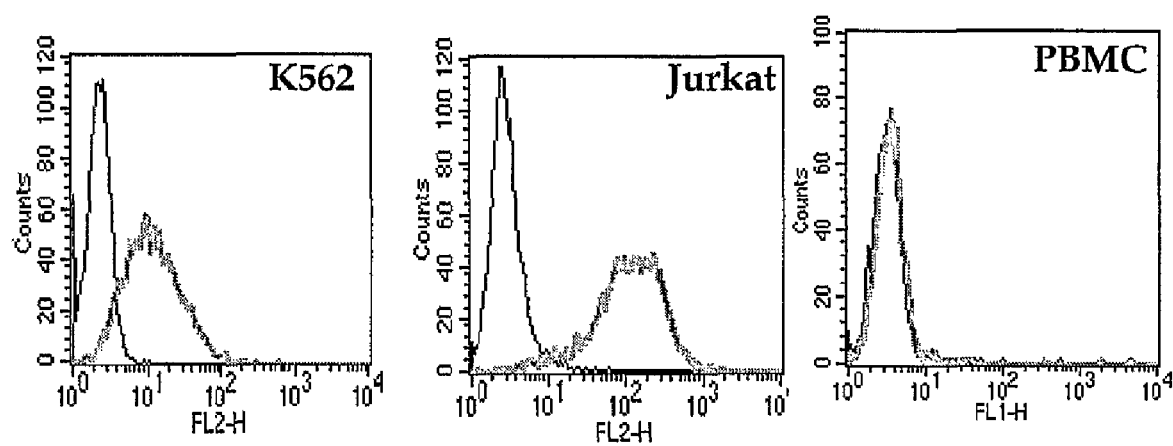

FIG. 10. Cell surface expression of NKp44L of different human cells

Cell surface expression of NKp44L of K562, Jurkat, and resting PBMC. The cells were incubated with 1 µg/ml of anti-NKp44L mAb anti-NKp44L mAb (grey thick line) or with the IgM isotype control (black thin), and analyzed by flow cytometry. Abscissa: NKp44L expression, Ordinates: number of cells.

DETAILED DESCRIPTION OF THE INVENTION

It has now been found according to the invention that a specific protein, termed NKp44L is expressed by the CD4+ T-cells form HIV-infected individuals whereas this protein is not expressed by the CD4+ T-cells from individuals which are not infected with HIV. The NKp44L protein is not expressed (i) in peripheral blood mononuclear cells (PBMC) from HIV-infected patients that do not express the CD3 antigen, (ii) in PBMC form HIV-infected patients that express the CD3 antigen but not the CD4 antigen, nor (iii) in PBMC from HIV-infected patients expressing the CD8 antigen. Particularly, the expression level of the NKp44L protein is further enhanced in activated CD4+ T-cells, such as PHA-activated CD4+ T-cells, from HIV-infected individuals.

Further, it has been shown according to the invention that an increasing expression level of the NKp44L protein is correlated with the decrease in the number of CD4+ T-cells which is observed in HIV-infected patients, thus in patients undergoing a progression of AIDS. Consequently, the expression level of the NKp44L protein is indicative of the immunological status of an HIV-infected patient.

Additionally, it has been found according to the invention that an increase in the expression of the NKp44L protein is correlated with an increasing HIV viral load within the patients tested. Thus, the expression level of the NKp44L protein is also indicative of the status of the replicative activity of the HIV virus within the infected patients.

In another aspect, it has also been found according to the invention that CD4+ T-cells from HIV-infected patients, and especially CD4+ T-cells that express the NKp44L protein, consist of specific targets for their cytolysis by Natural Killer (NK) cells, particularly activated NK cells, and especially autologous NK cells from the same patient.

Importantly, the present inventors have shown that the NK cells of an HIV-infected individual are activated specifically, through a non-MHC dependent triggering mechanism, by the autologous CD4+ T-cells that express the NKp44L protein.

Consequently, it has been determined according to the present invention that the NKp44L expression by the CD4+ T-cells of patients infected with HIV is of a high biological relevance in the context of AIDS disease progression, and especially as regards the evolution of immunodeficiency which parallels the occurrence of the various AIDS-related diseases.

In other words, there has been found according to the invention a statistically significant correlation between the expression level of the NKp44L protein at the membrane surface of the CD4+ T-cells collected from HIV-infected individuals and the progression or advancement status of the infectious disease, especially as regards the development of the patient's immunodeficiency caused by the progressive depletion of his CD4+ T-cells.

It flows from the experimental results obtained by the inventors which are briefly described above that the expression level of the NKp44L protein within the PBMC, and more specifically the expression level of the NKp44L protein by the CD4+ T-cells contained in the PBMC cell population, reveals itself to consists of an accurate biological marker of the progression status of the infection of an individual with an HIV virus. Further, the expression level of the NKp44L protein consists of a novel biological marker of the state of advancement of the HIV infection endowed with a very high biological significance, since it has been shown by the inventors that NKp44L expressed by the CD4+ T-cells triggers the autologous NK cells and activate these NK cells for specific cytolysis of the CD4+ T-cells, through a non-MHC dependent recognition of the CD4+ T-cells by the activated NK cells. In this particular context, the NKp44L protein expressed by the CD4+ T-cells of the HIV-infected patient activate the NK cells through the specific binding of the NKp44L protein to its specific receptor counterpart which is expressed at the membrane surface of the NK cells, namely the NKp44 receptor protein which has already been described by Cantoni et al. (1999) and by Vitale et al. (1998).

Further, the NKp44L protein has formerly been isolated by another inventive entity and this protein has already been shown to be expressed in various kinds of tumour cell lines. Still further, the NKp44L expressed by certain tumour cells has been shown to be a ligand that specifically binds to the NKp44 receptor protein cited above, which receptor protein is expressed by the NK cells, including the activated NK cells. It has also been formerly shown by this other inventive entity that the NKp44 receptor protein that is expressed by the activated NK cells might be responsible for at least part of the tumour cells cytolysis effected by the activated NK cells (unpublished information).

Taken together, the results obtained by the inventors have allowed them to carry out various methods which make use of the NKp44L protein as a novel biologically relevant marker of the disease progression for individuals that are already diagnosed as having been infected by HIV.

Further, the inventors have surprisingly found that a specific polypeptide, derived from the gp41 protein from HIV, markedly enhances the expression of the Nkp44L protein at the membrane surface of CD4+ T-cells.

It has also been determined according to the present invention that the lysis by the NK cells of the CD4+ T-cells from patients infected with HIV depends on that specific HIV polypeptide.

HIV-1 gp41 is composed of three domains, an extracellular domain (ectodomain), a transmembrane domain and an intracellular domain (endodomain). The gp41 ectodomain contains three major functional regions, i.e., the fusion peptide located at the N-terminus of gp41, followed by two 4-3 heptad repeats adjacent to the N- and C-terminal portions of the gp41 ectodomain, designated NHR (N-terminal heptad repeat) and CHR (C-terminal heptad repeat), respectively. The N- and C-terminal repeats are also named as "HR1" and "HR2".

Both NHR and CHR regions function as essential structures required for conformational changes during the process of membrane fusion between HIV-1 and CD4+ T cells.

Surprisingly, the inventors have found that a short peptide, derived from the gp41 protein, which is located between the well-known HR1 and HR2 regions, induces the surface expression of NKp44L on CD4+ T cells.

In other words, the inventors have identified a short peptide derived from the gp41 protein of HIV, which is responsible for the NKp44L surface expression and thus also for the lysis of CD4+ T cells by the endogenous NK cells.

These results obtained by the inventors have allowed them to carry out screening methods, which make use of a specific peptide derived from gp41 as a new target for therapeutical agents, distinct from the well known HR1 and HR2 regions.

Importantly, the present inventors have also shown that the protein NKp44L is expressed on tumor cell surface and that this expression of NKp44L is induced or enhanced by said short peptide derived from gp41.

Thus according to the invention, said short peptide derived from gp41 can be used for expressing NKp44L at the surface of tumor cells and then induce their specific lysis by NK cells.

Accordingly, the invention concerns therapeutical methods, and pharmaceutical compositions, comprising a polypeptide as briefly described above, for manufacturing anti-cancer pharmaceutical compositions.

Screening methods and related compositions above mentioned, will be described in details, in the part entitled "Further methods and compositions according to the invention".

In Vitro Diagnosis Methods of the Invention.

A first object of the present invention consists of a method for the in vitro assessment of the progression status of the infection of an individual with an HIV virus, wherein said method comprises the steps of:
  (a) incubating said biological sample with a ligand compound which specifically binds onto the NKp44L protein of SEQ ID No1, or onto the extracellular domain portion thereof; and
  (b) measuring the amount of said ligand compound which is bound to the CD4+ T cells, whereby said measured amount of said bound ligand compound is indicative of the progression status of the viral infection.

As used herein an "HIV" virus consists of either an HIV-1 or an HIV-2 virus, and more particularly any virus strain or isolate of an HIV-1 or an HIV-2 virus.

As used herein, the "assessment of the progression status" of the infection consists of raw experimental data indicative of the immunological status of the HIV-infected patient tested, since, as already mentioned above, there is a statistically relevant correlation between (A) the expression of the NKp44L protein at the cell surface of the CD4+ T-cells and (B) (i) the rate of CD4+ T-cells of said patient or (ii) the level of NK cells cytolysis activity against the CD4+ T-cells of said patient. Thus, according to the invention, the more NKp44L protein is expressed by the CD4+ T-cells, the more the HIV disease has progressed within said patient. Indeed, the sole measurement of the expression level of the NKp44L protein might not be sufficient for a global accurate clinical diagnosis, or prognosis, of the progression status of the disease within the patient tested. Thus the measurement of the expression level of the NKp44L might be completed by, or combined with, other diagnosis or prognosis markers of the disease, for example one of the prior art markers that have previously been cited in the present specification.

As used herein, the "extracellular domain portion" of the NKp44L protein of SEQ ID No1 consists of a polypeptide comprising the amino acid sequence starting from the amino acid located in position 928 and ending at the amino acid in position 1168 of the amino acid sequence SEQ ID No1.

As used herein, the "ligand compound" consists of any molecule, either (i) a naturally occurring or naturally produced molecule which has been purified from its biological environment or (ii) a molecule that has been manufactured by partial biological or chemical synthesis (hemi-synthesis) or (iii) a molecule that has been prepared by complete biological or chemical synthesis. Said ligand compound must bind specifically (selectively) to the NKp44L protein, which means, in the context of the present invention, that said ligand compound, when incubated in a biological sample containing human cells, exclusively binds to the NKp44L expressed by at least some of these human cells, and thus conversely does not bind in a detectable manner to proteins expressed by these cells which are distinct from NKp44L or from the portion of the NKp44L protein which is exposed at the membrane surface of the $CD4^+$ T-cells. Most preferably, the biological sample is selected from the group consisting of (i) a sample of whole blood, (ii) a suspension of peripheral mononuclear and polymorphonuclear cells purified from a whole blood sample, (iii) a suspension of peripheral blood mononuclear cells (PBMC) purified from a whole blood sample, (iv) a suspension of T cells purified from a whole blood sample and (v) a suspension of $CD4^+$ T-cells purified from a whole blood sample.

As used herein, the "amount" of the ligand compound that is bound to the $CD4^+$ T-cells mainly means the ratio or percentage of $CD4^+$ T-cells contained in the assay biological sample that bind said ligand compound or, in other words, the ratio of $CD4^+$ T-cells contained in the assay biological sample that express the NKp44L protein. In another embodiment, for measuring the "amount" of said ligand compound that is bound to the $CD4^+$ T-cells, it is also taken into account the amount of the ligand compound, for example the number of ligand compound molecules, that is bound to each cell expressing the NKp44L protein. Illustratively, the "amount" of said ligand compound which is bound to the $CD4^+$ T-cells can be expressed as the ratio, preferably the percentage, of the CD4+ T-cells contained in the assay sample for which the expression of the NKp44L protein at their membrane surface is detectable through the specific binding of said ligand compound onto the expressed KNp44L protein.

Because it has been shown by the inventors that there is a correlation between the expression level of the NKp44L protein by the $CD4^+$ T-cells of an HIV-infected patient and the number of $CD4^+$ T-cells of said patient, another object of the present invention consists of a method for the in vitro determination of the ratio of $CD4^+$ T cells present in a biological sample containing blood cells collected from a patient infected with an HIV virus, wherein said method comprises the steps of:
  (a) incubating said biological sample with a ligand compound which specifically binds onto the NKp44L protein of SEQ ID No1, or onto the extracellular domain portion thereof; and
  (b) measuring the amount of said ligand compound which is bound to the $CD4^+$ T cells, whereby said measured amount of said bound ligand compound is indicative of the rate of $CD4^+$ T cells contained in said biological sample.

As used herein, the "rate" of $CD4^+$ T-cells contained in the assay biological sample consists of the number of $CD4^+$ T-cells which are found in the initial volume of whole blood from which the assay biological sample has been prepared. For example, the rate of the $CD4^+$ T-cells may be expressed as the number of $CD4^+$ T-cells per $mm^3$ of the initial whole blood sample which was used for preparing said biological sample.

Figure 1:
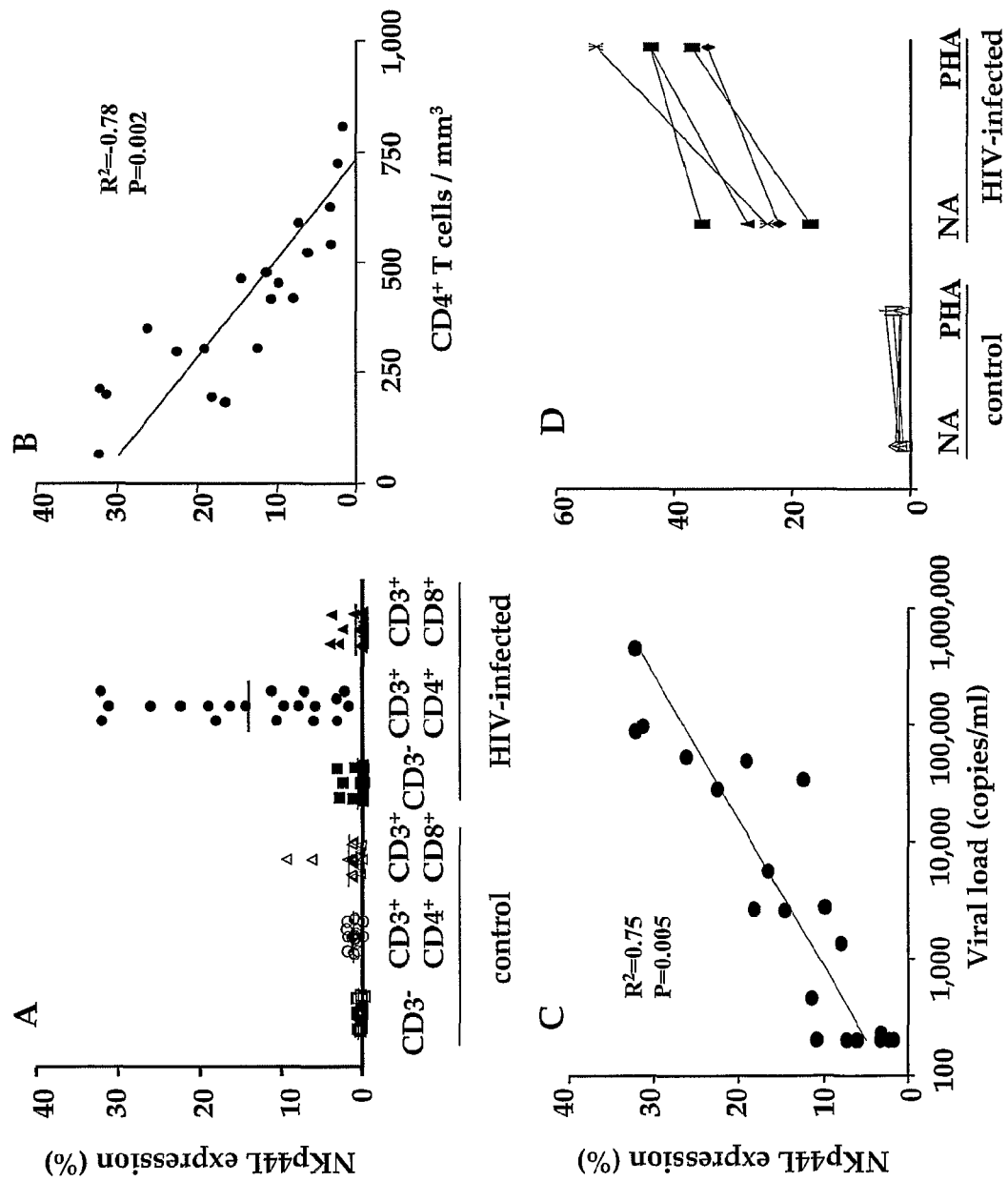
FIG. 1. Expression of NKp44L in CD4$^+$ T cells from HIV-infected individuals is associated with disease stage.

According to the method above, the rate of the $CD4^+$ T-cells of the patient which is tested can easily be determined by the one skilled in the art, for example by referring to a standard control curve wherein each $CD4^+$ T-cell rate value is plotted against the NKp44L expression level values obtained from previous or simultaneous assays, as shown in the examples herein. In this embodiment, the one skilled in the art first measures the NKp44L expression level according to the method above and then determines, from the standard control curve, the corresponding $CD4^+$ T-cell rate. For example, the one skilled in the art can use, as the standard curve, the one which is shown in FIG. 1B.

Since, as already disclosed above, the case definition of AIDS in adults and adolescents is now expanded to include HIV infection in an individual with $CD4^+$ T-cell count less than 200 cells per $mm^3$, and that there is a strict correlation between the rate of $CD4^+$ T-cells in an HIV-infected individual and the expression level of the NKp44L protein by said $CD4^+$ T-cells, then the progression status of the disease in an HIV-infected individual can be pertinently assessed by measuring said NKp44L expression level, by measuring the amount of the ligand compound defined above which is bound to the $CD4^+$ T-cells of said individual, through performing the first method described above. For example, a given patient will be included as consisting a case of AIDS, if the value of the expression level of the NKp44L protein is more than 20 percent of the CD4+ T-cells of the assay biological sample that express the NKp44L protein, as revealed by the specific binding of the ligand compound onto the expressed KNp44L protein, since the 20 percent amount value corresponds to less than 200 CD4+ T-cells per mm3, as shown in FIG. 1B.

Because it has been shown that there is a correlation between the expression level of the NKp44L protein by the $CD4^+$ T-cells of an HIV-infected patient and the HIV viral load in said patient, a further object of the invention consists of a method for the in vitro determination of the HIV viral load of a biological sample containing blood cells collected from a patient infected with a HIV virus, wherein said method comprises the steps of:
  (a) incubating said biological sample with a ligand compound which specifically binds onto the NKp44L protein of SEQ ID No1, or onto the extracellular domain portion thereof; and
  (b) measuring the amount of said ligand compound which is bound to the $CD4^+$ T cells, whereby said measured amount of said bound ligand compound is indicative of the HIV viral load of said biological sample.

According to the method above, the HIV viral load of the patient which is tested can easily be determined by the one skilled in the art, for example by referring to a standard control curve wherein each HIV viral load value is plotted against the NKp44L expression level values obtained from previous or simultaneous assays, as shown in the examples herein. In this embodiment, the one skilled in the art first measures the NKp44L expression level according to the method above and then determines, from the standard control curve, the corresponding HIV viral load. For example, the one skilled in the art may use, as the standard curve, the one which is shown in FIG. 1C.

In a preferred embodiment of any one of the methods described above, the biological sample is selected from the group consisting of (i) a sample of whole blood, (ii) a suspension of peripheral mononuclear and polymorphonuclear cells purified from a whole blood sample, (iii) a suspension of peripheral blood mononuclear cells (PBMC) purified from a whole blood sample, (iv) a suspension of T cells purified from a whole blood sample and (v) a suspension of CD4+ T-cells purified from a whole blood sample, for example according to the method taught in the examples herein.

In a first preferred embodiment of the ligand compound used in any one of the methods above, said ligand compound consists of an antibody directed to the NKp44L protein of SEQ ID No1 or of an antibody directed to the extracellular domain portion thereof. According to this first preferred embodiment, said ligand compound consists of a ligand compound produced by partial or complete biological synthesis, as defined previously.

Said anti-NKp44L antibody may consist of a polyclonal antibody which may be obtained by (i) administering an immunologically effective amount of the purified NKp44L protein to an animal, preferably in combination with an adjuvant of immunity, such as the Freund's complete adjuvant, (ii) then collecting the whole blood of the immunised animal and (iii) purifying the anti-NKp44L polyclonal antibodies, such as for example by using an immunoaffinity chromatographic substrate onto which has previously been immobilised the purified NKp44L protein. These techniques for obtaining purified polyclonal antibodies are well known from the one skilled in the art.

Said anti-NKp44L antibody may consist of a polyclonal antibody, in which case said antiNKp44L antibody may be prepared from hybridomas obtained after fusion of B cells of animals immunised against the purified NKp44L protein with myeloma cells, according to the well known technique described by Kohler and Milstein in 1975.

Said anti-NKp44L antibody may also consist of an antibody which has been produced by the trioma technique or by the human B-cell hybridoma technique described by Kozbor et al. in 1983.

Said anti-NKp44L antibody may also consist of single chain Fv antibody fragments (U.S. Pat. No. 4,946,778; Martineau et al., 1998), of antibody fragments obtained through phage display libraries (Ridder at al., 1995) or of humanized antibodies (Reinmann et al., 1997; Leger et al., 1997).

Most preferably, the anti-NKp44L antibody consists of a monoclonal antibody which is obtained by the following steps:
  (i) preparing a batch of purified recombinant NKp44L protein of SEQ ID No1;
  (ii) immunizing mice, for example BALB/c mice, with an effective amount of the purified NKp44L protein provided at step (ii), for example through three successive injection of said purified protein, each spaced by a one month time period
  (iii) preparing hybridoma cell lines by fusion of the purified B cells of the mice immunised at step (ii), for example using the ClonaCell-HY hybridoma cloning kit according to the manufacturer's instructions (StemCell Technologies Inc., Vancouver, BC, Canada);
  (iv) culturing clones of the hybridoma cell lines prepared at step (iii) and selecting the clone(s) which secrete a monoclonal antibody directed against the NKp44L protein; and
  (v) purifying the monoclonal antibodies produced by the hybridoma cell clones which have been selected at step (iv).

A most preferred hybridoma cell clone producing an anti-NKp44L monoclonal antibody consists of the hybridoma cell line NKp44L #7.1. Anti-NKp44 and anti-NKp44L monoclonal antibodies are preferably prepared such as taught in the examples.

For preparing a batch of purified recombinant KNp44L protein of SEQ ID No1 at step (i) of the method above, the one skilled in the art may perform a method comprising the following steps:
  (i) transfecting a recipient cell host, preferably a mammal cell line such as COS-7 cells, with an expression vector into which has been inserted a nucleic acid encoding the Nkp44L protein of SEQ ID No1, preferably a nucleic acid of SEQ ID No3, or a polypeptide comprising the extracellular domain thereof, and wherein said nucleic acid is operably linked to expression signals comprising at least a promoter which is functional in said recipient cell host, so that the resulting transfected cell host actually produces the NKp44L protein, when place in appropriate culture conditions;
  (ii) culturing the transfected cell host in an appropriate culture medium, so that the NKp44L protein, or the extracellular portion thereof, is produced;
  (iii) collecting the NKp44L protein, or the extracellular portion thereof, from the cell culture supernatant or from the cell lysate of the cultured transfected cell host;
  (iv) purifying the NKp44L protein, or the extracellular portion thereof, collected at step (iii), for example through immunoaffinity chromatographic substrate onto which anti-NKp44L antibodies, or alternatively purified NKp44 proteins, have previously been immobilised.

A preferred method for preparing purified NKp44L is shown in the examples herein.

In a second embodiment of the ligand compound used in any one of the methods above, said ligand compound consists of the purified NKp44 protein of SEQ ID No2, or a polypeptide comprising the extracellular domain portion thereof. This second embodiment illustrates a further embodiment wherein the ligand compound is produced through complete biological synthesis.

As used herein, the extracellular domain portion of the NKp44 protein is located in the N-terminal part of the NKp44 protein of SEQ ID No2 and consists of the amino acid sequence starting from the amino acid residue in position 22 and ending at the amino acid residue in position 169 of SEQ ID No2.

For producing the NKp44 protein, or the extracellular domain portion thereof, under a purified form, the one skilled in the art will advantageously refer to the methods disclosed by Cantoni et al. (1999). For example, the NKp44 recombinant protein may be prepared under a purified form through the following steps:
  (i) transfecting a recipient cell host, preferably a mammal cell line such as COS-7 cells, with an expression vector into which has been inserted a nucleic acid encoding the Nkp44 protein of SEQ ID No2, preferably a nucleic acid of SEQ ID No4, or a polypeptide comprising the extracellular domain thereof, and wherein said nucleic acid is operably linked to expression signals comprising at least a promoter which is functional in said recipient cell host, so that the resulting transfected cell host actually produces the NKp44 protein, when place in appropriate culture conditions;
  (ii) culturing the transfected cell host in an appropriate culture medium, so that the NKp44 protein, or the extracellular portion thereof, is produced;
  (iii) collecting the NKp44 protein, or the extracellular portion thereof, from the cell culture supernatant or from the cell lysate of the cultured transfected cell host;
  (iv) purifying the NKp44 protein, or the extracellular portion thereof, collected at step (iii), for example through immunoaffinity chromatographic substrate onto which anti-NKp44 antibodies, or alternatively purified NKp44L proteins, have previously been immobilised.

For performing the measure of the amount of said ligand compound that has bound to the CD4+ T-cells, at step (b) of any one of the methods described above, it is most preferred that said ligand compound is labelled with a detectable molecule, so that the measure consists of detecting a physical signal produced by said detectable molecule, and wherein the value of said physical signal which is obtained reflects the amount of said ligand compound which is bound to the NKp44L protein expressed by the CD4+ T-cells contained in the biological sample initially collected from the HIV-infected patient.

According to a first preferred aspect, said detectable molecule consists of a radioactive molecule, for example when the ligand compound is itself radioactively labelled, through conventional techniques or also when the ligand compound also binds to a radioactively labelled detectable molecule.

According to this first preferred aspect, said radioactive molecule is labelled with a radioactive isotope selected from the group consisting of [$^{32}$P], [$^{3}$H] and [$^{35}$S].

According to a second preferred aspect, said detectable molecule consists of a fluorescent molecule.

According to this second preferred aspect, said fluorescent molecule is most preferably selected from the group consisting of Green Fluorescent protein (GFP) and the Yellow Fluorescent Protein (YFP), which are both well known from the one skilled in the art. Illustratively said fluorescent molecule consists of the fluoreporter FITC protein and for labelling, it may be used for FITC labelling kit which is marketed by Molecular Probes Inc. (U.S.A.).

According to a third preferred aspect, said detectable molecule consists of a luminescent molecule.

According to this third preferred embodiment, said luminescent molecule is most preferably selected from the group consisting of luciferase.

According to a fourth preferred aspect, said detectable molecule consists of a receptor that is selectively recognised by a ligand molecule.

According to this fourth preferred aspect, said detectable molecule consists of a biotin, most preferably under the form of a biotinylated ligand compound, in which case the corresponding ligand molecule consists of a molecule containing an avidin or a straptavidin, said ligand molecule being either (i) radioactively labelled, (ii) fluorescent or (iii) luminescent, so that the physical signal which is detected for measuring the expression level of the NKp44L protein by the CD4+ T-cells can be produced.

At step (b) of any one of the methods according to the invention, the measure of the amount of the ligand compound that is bound to the NKp44L protein expressed by the CD4+ T-cells contained in the assay sample can be carried out using any one of the various techniques allowing the measure of the binding of a compound, and especially of a detectable compound, onto the membrane surface of cells, which are already available to the one skilled in the art.

Most preferably, step (b) of any one of the methods above is carried out by performing a flow cytometry analysis of the biological sample, using various detectable markers, most preferably various fluorescent markers, including the detectable ligand compound that specifically binds to the NKp44L protein.

In a preferred embodiment, the flow cytometry analysis is performed with at least two detectable markers, most preferably two fluorescent markers, respectively (i) the detectable ligand compound that specifically binds onto the NKp44L protein, or onto the extracellular domain portion thereof, and (ii) a detectable marker that binds specifically onto the CD4 antigen, most preferably an antibody directed against the CD4 antigen. Most preferably, (i) the detectable ligand compound is fluorescently labelled so as to emit a fluorescent signal at a first given wavelength upon appropriate light excitation and (ii) the detectable marker that binds to the CD4 antigen is fluorescently labelled so as to emit a fluorescent signal at e second given wavelength, distinct from the first given wavelength, upon appropriate light excitation.

When using the combination of two detectable markers above, (i) the total number of CD4+ T-cells contained in the assay biological sample is determined by counting, by two-color flow cytometric analysis, the number of cells that emit light at the second given wavelength corresponding to the fluorescently labelled marker that binds to the CD4 antigen, and (ii) the number of cells contained in the assay biological sample that express the NKp44L protein is determined by counting, by two-color flow cytometric analysis, the number of cells that emit light at the first given wavelength corresponding to the fluorescently labelled ligand compound that specifically binds to the NKp44L protein, so that the ratio of CD4+ T-cells from the sample that express the NKp44L protein is then calculated.

In a first specific embodiment of the two-color flow cytometric analysis measuring method above, the ratio of the CD4+ T-cells that express the NKp44L protein is determined by the simultaneous detection of emitting light at (i) the second given wavelength corresponding to the fluorescently labelled marker that binds to the CD4 antigen and at (ii) the first given wavelength corresponding to the fluorescently labelled compound that binds to the NKp44L protein, so that the ratio of CD4+ T-cells from the sample that express the NKp44L protein is then directly calculated.

In a second preferred embodiment of any one of the methods of the present invention, step (b) of measuring the amount of said ligand compound which is bound to the CD4+ T cells consists of a numbering of the cells contained in said biological sample onto which is bound said ligand compound by microscopy, including confocal microscopy. According to this second preferred embodiment, the reagents for carrying out the measures are preferably the same as those which are described above for performing the flow cytometric analysis.

Another object of the invention consists of a kit for the in vitro assessment of the progression status of the infection of an individual with an HIV virus, wherein said kit comprises:
  (i) a ligand compound that specifically binds to the NKp44L protein of SEQ ID No1, or to the extracellular domain portion thereof;
  (ii) a marker molecule that specifically binds to the CD4 antigen.

The kit as defined above may also be used for, respectively:
  (i) the in vitro determination of the ratio of CD4+ T cells present in a biological sample containing blood cells collected from a patient infected with an HIV virus; and for
  (ii) the in vitro determination of the HIV viral load of a biological sample containing blood cells collected from a patient infected with a HIV virus.

In the kits of the invention above, the ligand compound encompass the various embodiments of said ligand compound that have been previously described in the present specification.

In the kits of the invention above, the marker molecule that specifically binds to the CD4 antigen encompass the various embodiments of said marker molecule compound that have been previously described in the present specification.

Most preferably, both (i) the ligand compound and (ii) the marker molecule are differentially fluorescently labelled, as already described above.

Most preferably, the labelled ligand compound consists of a labelled monoclonal antibody that specifically binds to the NKp44L protein of SEQ ID No1, or to the extracellular domain portion thereof.

Most preferably, the labelled marker molecule consists of an anti-CD4 monoclonal antibody, such as that which is available at the American Type Culture Collection under the accession number ATTC-CRL-8002.

As it will be detailed hereunder, the experimental results obtained according to the present invention extend to the therapeutical field for the treatment of an infection with an HIV virus and the present invention thus also relates to methods for the screening of therapeutically active compounds, to pharmaceutical compositions as well as to methods for treating patients which are infected with HIV.

Screening Methods, Pharmaceutical Compositions and Methods of Treatment of the Invention.

It has been shown according to the invention that the non-MHC dependent NK cells cytolysis against the CD4+ T-cells that express the NKp44L protein is blocked when the binding between the NKp44L protein expressed by the CD4+ T-cells and the NKp44 receptor protein expressed by the activated NK cells is prevented.

More specifically, it is shown in the examples that the non-MHC dependent NK cells cytolysis against the CD4+ T-cells that express the NKp44L protein is blocked when a monoclonal antibody directed against the NKp44L protein is added to a whole blood cell suspension collected from an HIV-infected patient. These experimental results obtained by the inventors mean that the binding of the monoclonal antibody above to the NKp44L protein which is expressed at the membrane surface of the CD4+ T-cells prevents the recognition of the CD4+ T-cells from the HIV-infected patient by the NK cells, through the specific binding of the NKp44 receptor protein to the NKp44L protein, thus efficiently preventing the CD4+ T-cells cytolysis by said NK cells that would otherwise occur, whereby the immunodeficiency of the HIV-infected patient develops.

Thus, it is shown according to the invention that any compound that biologically acts by preventing the specific binding of the NKp44 receptor protein of NK cells to the NKp44L protein of CD4+ T-cells is useful as a therapeutical agent that inhibits or blocks the CD4+ T-cell cytolysis by the NK cells in individuals infected with an HIV virus. More specifically, any compound that prevents the specific binding of the NKp44 receptor protein of NK cells to the NKp44L protein of CD4+ T-cells, either (i) by binding specifically to the NKp44 receptor protein expressed by the NK cells or (ii) by binding specifically to the NKp44L protein expressed by the CD4+ T-cells of the HIV-infected patient is useful as a therapeutical agent that inhibits or blocks the CD4+ T-cell cytolysis by the NK cells in individuals infected with an HIV virus.

Thus, according to the invention, any of such therapeutically useful agent or compound can be effectively screened by any method wherein the binding or the absence of binding between the NKp44 receptor protein and the NKp44L protein is detected.

Screening Methods of the Invention.

Thus, another object of the present invention consists of a method for the in vitro screening of compounds for preventing or treating a disease linked with the infection of an individual with an HIV virus, wherein said method comprises the steps of:

(a) incubating a candidate compound to be tested with a screening system in a liquid solvent, wherein said screening system comprises:
  (i) a first partner exposing to the solvent a plurality of molecules of the NKp44L protein of SEQ ID No1, or a plurality of molecules of a polypeptide comprising the extracellular domain portion thereof;
  (ii) a second partner exposing to the solvent a plurality of molecules of the NKp44 receptor protein of SEQ ID No2, or a plurality of molecules of a polypeptide comprising the extracellular domain portion thereof;
  wherein (iii) the plurality of molecules of the NKp44L protein of SEQ ID No1, or the plurality of molecules of a polypeptide comprising the extracellular domain portion thereof, on one hand, and (iv) the plurality of molecules of the NKp44 receptor protein of SEQ ID No2, or the plurality of molecules of a polypeptide comprising the extracellular domain portion thereof, on second hand, are able to bind one to each other;
(b) quantifying the binding of (iii) the plurality of molecules of the NKp44L protein of SEQ ID No1, or the plurality of molecules of a polypeptide comprising the extracellular domain portion thereof to (iv) the plurality of molecules of the NKp44 receptor protein of SEQ ID No2, or the plurality of molecules of a polypeptide comprising the extracellular domain portion thereof;
(c) comparing the binding which is quantified at step (b) with the binding which is quantified when step (a) is performed in the absence of said candidate compound;
(d) selecting positively the candidate compound as a therapeutical agent when said candidate compound inhibits or blocks the binding of (iii) the plurality of molecules of the NKp44L protein of SEQ ID No1, or the plurality of molecules of a polypeptide comprising the extracellular domain portion thereof to (iv) the plurality of molecules of the NKp44 receptor protein of SEQ ID No2, or the plurality of molecules of a polypeptide comprising the extracellular domain portion thereof.

In the screening system above, the liquid solution, wherein said liquid solution may also be termed the "solvent", is preferably an aqueous solution, including a saline aqueous solution, and wherein said saline aqueous solution encompass any appropriate medium for culturing cells, preferably mammalian cells, and most preferably human cells.

In the screening system which is used when performing the screening method above, the first and second "partners" are independently selected from the group consisting of (i) a plurality of molecules of the NKp44L protein of SEQ ID No1, or a plurality of molecules of a polypeptide comprising the extracellular domain portion thereof or alternatively a plurality of molecules of the NKp44 receptor protein of SEQ ID No2, or a plurality of molecules of a polypeptide comprising the extracellular domain portion thereof, or (ii) a substrate material onto which is bound a plurality of molecules of the NKp44L protein of SEQ ID No1, or a plurality of molecules of a polypeptide comprising the extracellular domain portion thereof or alternatively a plurality of molecules of the NKp44 receptor protein of SEQ ID No2, or a plurality of molecules of a polypeptide comprising the extracellular domain portion thereof, wherein said substrate material encompasses cells that express at their membrane surface, in a manner exposed to the solvent, a plurality of molecules of the NKp44L protein of SEQ ID No1, or a plurality of molecules of a polypeptide comprising the extracellular domain portion thereof or alternatively a plurality of molecules of the NKp44 receptor protein of SEQ ID No2, or a plurality of molecules of a polypeptide comprising the extracellular domain portion thereof.

The candidate compounds which may be screened according to the screening method above may be of any kind, including, without being limited to, natural or synthetic compounds or molecules of biological origin such as polypeptides.

In a particular embodiment of the screening method, the candidate compound consists of the expression product of a DNA insert contained in a phage vector, such as described by Parmley and Smith (1988). Specifically, random peptide libraries are used. The random DNA inserts encode for peptides of 8 to 20 amino acids in length (Oldenburg et al., 1992; Valadon et al., 1996; Lucas, 1994; Westerink, 1995; Felici et al., 1991). According to this particular embodiment, the recombinant phages expressing a polypeptide that specifically binds either (i) to the NKp44L protein of SEQ ID No1, or to the extracellular domain portion thereof, or (ii) to the NKp44 receptor protein of SEQ ID No2, or to the extracellular domain portion thereof, is retained as a candidate compound for use in the screening method above.

Candidate compounds for use in the screening method above can also be selected by any immunoaffinity chromatography technique using any chromatographic substrate onto which (i) molecules of the NKp44L protein of SEQ ID No1, or of a polypeptide comprising the extracellular domain portion thereof, or (ii) molecules of the NKp44 receptor protein of SEQ ID No2, or of a polypeptide comprising the extracellular domain portion thereof, have previously been immobilised, according to techniques well known from the one skilled in the art.

In a first preferred embodiment of the screening method above, the screening system used in step (a) includes the use of an optical biosensor such as described by Edwards and Leatherbarrow (1997) or also by Szabo et al. (1995). This technique permits the detection of interactions between molecule in real time, without the need of labelled molecules. This technique is based on the surface plasmon resonance (SPR) phenomenon. Briefly, a first protein partner molecule, either (i) the NKp44L protein of SEQ ID No1, or a polypeptide comprising the extracellular domain portion thereof, or (ii) molecules of the NKp44 receptor protein of SEQ ID No2, or a polypeptide comprising the extracellular domain portion thereof, is attached to a surface (such as a carboxymethyl dextran matrix). Then, the second protein partner molecule, either (iii) molecules of the NKp44 receptor protein of SEQ ID No2, or a polypeptide comprising the extracellular domain portion thereof or (iv) the NKp44L protein of SEQ ID No1, or a polypeptide comprising the extracellular domain portion thereof is incubated with said substrate, in the presence or in the absence of the candidate compound to be tested and the binding, including the binding level, or the absence of binding between the first and second protein partner molecules is detected. For this purpose, a light beam is directed towards the side of the surface area of the substrate that does not contain the sample to be tested and is reflected by said substrate surface. The SPR phenomenon causes a decrease in the intensity of the reflected light with a specific combination of angle and wavelength. The binding of the first and second protein partner molecules causes a change in the refraction index on the substrate surface, which change is detected as a change in the SPR signal.

According to the first preferred embodiment of the screening method above, the "first partner" of the screening system consists of the substrate onto which the first protein partner molecule is immobilised, and the "second partner" of the screening system consists of the second partner protein molecule itself.

In a second preferred embodiment of the screening method above, the "first partner" of the screening system consists of cells, advantageously mammal cells, preferably human cells, and most preferably NK cells, that express at their membrane surface a plurality of molecules of the NKp44L protein of SEQ ID No1, or a plurality of molecules of a polypeptide comprising the extracellular domain portion thereof and the "second partner" of the screening system consists of cells, advantageously mammal cells, preferably human cells, and most preferably CD4+ T-cells, that express at their membrane surface a plurality of molecules of the NKp44 receptor protein of SEQ ID No2, or a plurality of molecules of a polypeptide comprising the extracellular domain portion thereof.

The present invention is also directed to a kit for the in vitro screening of compounds for preventing or treating a disease linked with the infection of an individual with an HIV virus, wherein said kit comprises a screening system that comprises:
(i) a first partner exposing to the solvent a plurality of molecules of the NKp44L protein of SEQ ID No1, or a plurality of molecules of a polypeptide comprising the extracellular domain portion thereof;
(ii) a second partner exposing to the solvent a plurality of molecules of the NKp44 receptor protein of SEQ ID No2, or a plurality of molecules of a polypeptide comprising the extracellular domain portion thereof;
wherein (iii) the plurality of molecules of the NKp44L protein of SEQ ID No1, or the plurality of molecules of a polypeptide comprising the extracellular domain portion thereof, on one hand, and (iv) the plurality of molecules of the NKp44 receptor protein of SEQ ID No2, or the plurality of molecules of a polypeptide comprising the extracellular domain portion thereof, on second hand, are able to bind one to each other.

In the screening kit above, the first and the second partners are as defined previously for the first screening method above.

The present invention is also directed to a method for the in vitro screening of compounds for preventing or treating a disease linked with the infection of an individual with an HIV virus, wherein said method comprises the steps of:
(a) bringing into contact a first cell population consisting of human activated NK cells and a second cell population consisting of human CD4+ T-cells expressing the NKp44L protein in the presence of a candidate therapeutical compound to be tested;
(b) measuring the cytolysis of the CD4+ T-cells by the activated NK cells;
(c) comparing the cytolysis value obtained at step (b) with the cytolysis value obtained when step (a) is performed in the absence of the candidate compound;
(d) selecting the candidate compounds that inhibit or block the NK-mediated cytolysis of the CD4+ T-cells.

The second screening method above, despite it consists of an in vitro method, has the technical advantage to directly reflect the therapeutical potential of the candidate compound by directly evidencing the biological activity of said candidate compound, as regards preventing the CD4+ T-cells cytolysis by the activated NK cells.

The activated NK cells may consist of cells from a NK cell line, such as the NK92 cell line described by Gong et al. (1994) or may consist of a primary culture of normal human purified NK cells.

The CD4+ T-cells that express the NKp44L protein may consist of CD4+ T-cells, eventually under the form of a cell line, that have been transfected with a vector that allow the expression by said cells of the NKp44L protein, or may consist of CD4+ T-cells that were initially purified from a blood sample of an HIV-infected patient.

In a specific embodiment of the second screening method above, the activated NK cells and the CD4+ T-cells are autologous in that they both come from the same HIV-infected patient.

Preferably, the cytolysis measure consists of the conventional technique wherein the CD4+ T-cells, which are the target cells, are initially rendered radioactive with $^{51}$Cr, and wherein the cytolysis value consists of the percentage of cell lysis, as measured by the amount of $^{51}$Cr that is released in the cell culture medium by the lysed CD4+ T-cells.

Most preferably, the cytolysis value is obtained by assaying the cytolytic activity of the NK cells at increasing effector (NK cells) to target (CD4+ T-cells) ratios, for example from 1:1 to 50:1 effector: target cell ratios.

The candidate compounds that may be tested according to the second screening method above are the same than those that may be tested according to the first screening method that was described previously within the present specification.

Pharmaceutical Compositions and Methods of Treatment of the Invention.

A further object of the invention consists of a pharmaceutical composition for preventing or treating a disease linked to the infection of an individual with a virus of the HIV family, which comprises an effective amount of a ligand compound which is selected form the group consisting of (i) a ligand compound which specifically binds to the NKp44L protein of SEQ ID No1, or to the extracellular domain portion thereof and (ii) a ligand compound which specifically binds to the NKp44 protein of SEQ ID No2, or to the extracellular domain portion thereof, in combination with at least one physiologically acceptable excipient.

In a first preferred embodiment of the pharmaceutical composition above, said ligand compound consists of an antibody directed to the NKp44L protein of SEQ ID No1 or of an antibody directed to the extracellular domain portion thereof.

In a second preferred embodiment of the pharmaceutical composition above, said ligand compound consists of the NKp44 protein of SEQ ID No2, or a polypeptide comprising the extracellular domain thereof.

In a third preferred embodiment of the pharmaceutical composition above, said ligand compound consists of an antibody directed against the NKp44 protein of SEQ ID No2 or of an antibody directed against the extracellular domain portion thereof.

By "physiologically acceptable excipient or carrier" is meant solid or liquid filler, diluent or substance which may be safely used in systemic or topical administration. Depending on the particular route of administration, a variety of pharmaceutically acceptable carriers well known in the art include solid or liquid fillers, diluents, hydrotropes, surface active agents, and encapsulating substances. The amount of carrier employed in conjunction with the F(ab).sub.2 fragments to provide practical quantity of material per unit dose of composition.

Pharmaceutically acceptable carriers for systemic administration that may be incorporated in the composition of the invention include sugar, starches, cellulose, vegetable oils, buffers, polyols and alginic acid. Specific pharmaceutically acceptable carriers are described in the following documents, all incorporated herein by reference: U.S. Pat. No. 4,401,663, Buckwalter et al. issued Aug. 30, 1983; European Patent Application No. 089710, LaHann et al. published Sep. 28, 1983; and European Patent Application No. 0068592, Buckwalter et al. published Jan. 5, 1983. Preferred carriers for parenteral administration include propylene glycol, pyrrolidone, ethyl oleate, aqueous ethanol, and combinations thereof.

Representative carriers include acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol 9, oleyl alcohol, pectin, poly(acrylic acid) and its homologs, polyethylene glycol, polyvinyl alcohol, polyacrylamide, sodium lauryl sulfate, poly(ethylene oxide), polyvinylpyrrolidone, glycol monostearate, propylene glycol monostearate, xanthan gum, tragacanth, sorbitan esters, stearyl alcohol, starch and its modifications. Suitable ranges vary from about 0.5% to about 1%.

For formulating a pharmaceutical composition according to the invention, the one skilled in the art will advantageously refer to the last edition of the European pharmacopoeia or of the United States pharmacopoeia.

Preferably, the one skilled in the art will refer to the fourth edition "2002" of the European Pharmacopoeia, or also to the edition USP 25-NF20 of the United States Pharmacopoeia.

The weight amount of therapeutically active compound that is contained in each dose of the pharmaceutical composition of the invention will depend on the molecular weight of said therapeutically active compound as well as on the weight amount that is effective in blocking the cytolysis of the CD4+ T-cells by the NK cells in an HIV-infected patient.

For determining the appropriate amount of the therapeutically active compound, in a dose of a pharmaceutical composition of the invention, the one skilled in the art firstly determines the in vitro CD4+ T-cell cytolysis inhibiting ability of various weight amounts or concentrations of said therapeutically active compound, for example by performing the same steps (a) and (b) as in the second screening method of the invention which has been previously described herein, and then retain or select the given amount or concentration of said therapeutically active compound that blocks cytolysis. Then, the one skilled in the art transposes said retained or selected amount or concentration to the in vivo human situation, so that the concentration of said therapeutically active compound in the blood of a patient to which the pharmaceutical composition of the invention has been administered is identical to the concentration that blocks cytolysis in vitro.

The present invention is also directed to the use of a ligand compound which is selected form the group consisting of (i) a ligand compound which specifically binds to the NKp44L protein of SEQ ID No1, or to the extracellular domain portion thereof and (ii) a ligand compound which specifically binds to the NKp44 protein of SEQ ID No2, or to the extracellular domain portion thereof, for manufacturing a pharmaceutical composition for preventing or treating a disease linked to the infection of an individual with a virus of the HIV family.

This invention also deals with a method for preventing or for treating a disease linked to the infection of an individual with a virus of the HIV family, wherein said method comprises a step of administering to a patient in need of such treatment an effective amount of a ligand compound which is selected form the group consisting of (i) a ligand compound which specifically binds to the NKp44L protein of SEQ ID No1, or to the extracellular domain portion thereof and (ii) a ligand compound which specifically binds to the NKp44 protein of SEQ ID No2, or to the extracellular domain portion thereof.

Another object of the invention consists of a pharmaceutical composition for preventing or treating a disease linked to the infection of an individual with a virus of the HIV family, which comprises an effective amount of an antisense polynucleotide that specifically hybridises with the mRNA molecules encoding the NKp44I protein of SEQ ID No1, in combination with at least one physiologically acceptable excipient.

Preferably, said antisense polynucleotide is obtained by cloning, in the antisense orientation, the NKp44L fragment of SEQ ID No3, starting in position 1 and ending in position 902 of SEQ ID No3.

Thus, a preferred antisense polynucleotide consists of the nucleic acid which is complementary to the nucleic acid starting at the nucleotide n°1 and ending at the nucleotide n°902 of the nucleotide sequence SEQ ID No3.

This invention is also directed to the use of an antisense polynucleotide that specifically hybridises with the mRNA molecules encoding the NKp44I protein of SEQ ID No1 for manufacturing a pharmaceutical composition for preventing or treating a disease linked to the infection of an individual with a virus of the HIV family.

A further object of the invention consists of a method for preventing or for treating a disease linked to the infection of an individual with a virus of the HIV family, wherein said method comprises a step of administering to a patient in need of such treatment an effective amount of an antisense polynucleotide that specifically hybridises with the mRNA molecules encoding the NKp44I protein of SEQ ID No1.

Further Compositions and Screening Methods of the Invention

The inventors have surprisingly found that a specific polypeptide, derived from the gp41 protein of HIV, markedly enhances the expression of the Nkp44L protein on CD4+ T-cells surface. (example 6-8, below).

It has also been determined according to the present invention that the lysis of the CD4+ T-cells from patients infected with HIV by NK cells is directly related to the binding of said specific polypeptide on CD4+ T cells, with the simultaneous expression increase of NKp44L at their cell surface.

Accordingly, another object of the invention is a polypeptide comprising the following amino acid sequence:
$X_1X_2X_3X_4X_5X_6$SWSNKS$X_{13}X_{14}X_{15}X_{16}X_{17}$ (I) (SEQ ID NO: 5),
wherein $X_1$, $X_2$, $X_3$, $X_5$, $X_6$, $X_{13}$, $X_{15}$, $X_{16}$ and $X_{17}$ mean, independently one from each other, any amino acid residue, $X_4$ means any amino acid residue except A and W, and wherein $X_{14}$ means any amino acid residue except E and S.

The invention encompasses further polypeptides comprising the following amino acid sequence: PWASNASWSNKSLDDIW (II) (SEQ ID NO: 6).

A polypeptide, as defined above, is preferably derived from the gp41 protein and possesses at least 39, 40, 50, 60, 70, 80, 90, 100, 110, 120, 130, 140 or 150 consecutive amino acids of gp41 protein from HIV-1 and comprises the amino acid sequence of formula (I) above.

The polypeptide of formula (I) can be produced by recombinant DNA techniques, for example on the basis of the DNA sequence of gp41 protein from HIV1, or by chemical synthesis using standard peptide synthesis techniques.

Preferably, a polypeptide of formula (I) consists of the following amino acid sequence: PWASNASWSNKSLDDIW (II) (SEQ ID NO: 6).

The induction of NKp44L expression on CD4+ T-cells surface induced by the polypypetide of amino acid sequence (II) is illustrated in examples 6-8 below.

The high kinetics of the induction of the NKp44L expression at the cell surface is compatible with the induction of a translocation of a pre-synthesised NKp44L intracellular protein, from the cytoplasm towards the cell surface.

The invention also concerns a first method for the in vitro screening of compounds for preventing or treating a disease linked with the infection of an individual with an HIV virus, comprising the steps of:
(i) incubating a candidate compound to be tested with a polypeptide of formula (I),
(ii) assaying for the binding of the candidate compound to be tested with a polypeptide of formula (I).

The binding of the candidate compound to the polypeptide of formula (I) can be carried on by the one skilled in the art, for example by using a Two-hybrid system. Other means, known from the one skilled in the art can be used for the binding assays such as the use of bio sensor techniques (Edwards and Leatherbarrow (1997) or also by Szabo et al. (1995)), affinity chromatography, or High Throughput Screening (HTS), (Leblanc et al 2002).

The candidate compounds, which may be screened according to the screening method above, may be of any kind, including, without being limited to, natural or synthetic compounds or molecules of biological origin such as polypeptides.

Preferably, step (ii) consists of subjecting to a gel migration assay the mixture obtained at the end of step (i) and detecting the complexes formed between the candidate compound and the polypeptide of formula (I).

The gel migration assay can be carried out as known by the one skilled in the art.

The detection of the complexes formed between the complexes formed between the candidate compound and the polypeptide according to the invention can be easily observed by determining the stain position (protein bands) corresponding to the proteins analysed since the apparent molecular weight of a protein changes if it is part of a complex with another protein.

On one hand, the stains (protein bands) corresponding to the proteins submitted to the gel migration assay can be detected by specific antibodies for example antibodies specifically directed against a polypeptide of formula (I). One the other hand, a polypeptide of formula (I) can be tagged for an easier detection of the protein/candidate compound on the gel. For example, the polypeptide according to the invention can be fused to GST, HA, a poly-Histidine chain, or other detectable molecules in order to facilitate the identification of the different proteins on the gel.

The invention further concerns a second method for the in vitro screening of compounds for preventing or treating a disease linked to the infection of an individual with an HIV virus, comprising the steps of:
a) (i) bringing into contact a first CD4+ T-cell culture with a candidate compound, and HIV virus;
(ii) bringing into contact a second CD4+ T-cell culture with HIV virus, in the absence of said candidate compound; and
b) detecting the presence of NKp44L at the CD4+ T-cells surface issued from the culture (i) and (ii).

The detection of the presence of NKp44L at the CD4+ T-cells surface can be carried out as known by the one skilled in the art, for instance by a cytofluorometric analysis as it is described in the part Material and methods, corresponding to the example 6.

Preferably, the method described above, comprises an additional step (c) which consists of selecting positively the candidate compound as a therapeutical agent when the level of expression of NKp44L at the CD4+ T-cells surface issued from the culture (ii) is higher than the level of expression of NKp44L at the CD4+ T-cells surface issued from the culture (i).

The comparison of the level of expression of NKp44L at the CD4+ T-cells surface can be assessed by counting the number of CD4+ T cells expressing NKp44L on their surface, using a fluorescence activated cell sorter (FACS), as described in the corresponding Material and Methods section.

Alternatively, the detection of the presence of NKp44L at the CD4+ T-cells surface can be carried out indirectly, by measuring the NK lysis activity of CD4+ T cells, as it is described in the section Material and Methods, corresponding to the example 7.

This particular embodiment of the step (b) of the screening method above, despite it consists of an in vitro method, has the technical advantage to directly reflect the therapeutical potential of the candidate compound by directly evidencing the biological activity of said candidate compound, as regards preventing the CD4$^+$ T-cells cytolysis by the activated NK cells.

The activated NK cells may consist of cells from a NK cell line, such as the NK92 cell line described by Gong et al. (1994) or may consist of a primary culture of normal human purified NK cells.

The CD4$^+$ T-cells that express the NKp44L protein may consist of CD4$^+$ T-cells, eventually under the form of a cell line, that have been transfected with a vector that allow the expression by said cells of the NKp44L protein, or may consist of CD4$^+$ T-cells that were initially purified from a blood sample of an HIV-infected patient.

In a specific embodiment of the screening method above, the activated NK cells and the CD4$^+$ T-cells are autologous in that they both come from the same HIV-infected patient.

Preferably, the cytolysis measure consists of the conventional technique wherein the CD4$^+$ T-cells, which are the target cells, are initially rendered radioactive with $^{51}$Cr, and wherein the cytolysis value consists of the percentage of cell lysis, as measured by the amount of $^{51}$Cr that is released in the cell culture medium by the lysed CD4$^+$ T-cells.

Most preferably, the cytolysis value is obtained by assaying the cytolytic activity of the NK cells at increasing effector (NK cells) to target (CD4$^+$ T-cells) ratios, for example from 1:1 to 50:1 effector: target cell ratios.

Candidate compounds for use in the screening methods described immediately above can be selected among the candidate compounds which binds to one or several polypeptides of formula (I).

Accordingly, the invention also concerns a method for the in vitro screening of compounds for preventing or treating a disease linked with the infection of an individual with an HIV virus, comprising the steps of:
(i) submitting a candidate compound to the first screening method above, and
(ii) submitting a candidate compound positively selectionned at step (i) to the second screening method described immediately above.

Another object of the invention is a pharmaceutical composition for preventing or treating a disease linked to the infection of an individual with a virus of the HIV family, which comprises an effective amount of a ligand compound which specifically binds to the polypeptide of formula (I), in combination with at least one physiologically acceptable excipient.

Preferably, the physiologically acceptable excipients used for carrying out the pharmaceutical composition described above are the same than those that are described in the first part of the specification concerning ligands of NKp44L.

For formulating a pharmaceutical composition according to the present invention, the man skilled in the art will advantageously refer to the last edition of the European pharmacopoeia or of the United State pharmacopoeia.

For determining the appropriate amount of the therapeutically active compound, in a dose of a pharmaceutical composition of the invention, the one skilled in the art firstly determines the in vitro CD4$^+$ T-cell cytolysis inhibiting ability of various weight amounts or concentrations of said therapeutically active compound, for example by performing the screening method of the invention which has been previously described herein, and then retain or select the given amount or concentration of said therapeutically active compound that blocks cytolysis.

Then, the one skilled in the art transposes said retained or selected amount or concentration to the in vivo human situation, so that the concentration of said therapeutically active compound in the blood of a patient to which the pharmaceutical composition of the invention has been administered is identical to the concentration that blocks cytolysis in vitro.

Preferably, the ligand compound consists of an antibody directed to the polypeptide according to the invention.

Preferably, the ligand compound, or the pharmaceutical composition containing it, can be combined with a compound that inhibits the membrane fusion between HIV and CD4+ T cells. Such compounds are, for example, peptides derived from the HR1 or HR2 region of the gp41 protein and more precisely peptides referred to as T20, T21 or those described in U.S. Pat. No. 6,623,741.

This invention is also directed to the use of a ligand compound which specifically binds to the polypeptide of formula (I), for manufacturing a pharmaceutical composition for preventing or treating a disease linked to the infection of an individual with a virus of the HIV family.

Additionally, The inventors have also shown that the protein NKp44L is expressed on tumor cell surface, such as Jurkat cells and K562 cells.

They have also shown that a polypeptide of formula (I) induces the cell surface expression, of NKp44L by tumor cells, which then render these polypeptide-treated tumor cells susceptible to specific lysis by the NK cells.

Accordingly, the invention concerns methods and pharmaceutical compositions, comprising a polypeptide of formula (I), for treating cancer.

The invention concerns a pharmaceutical composition for treating a cancer, which comprises an effective amount of a polypeptide of formula (I), in combination with at least one physiologically acceptable excipient.

Preferably, the physiologically acceptable excipients used to carry out the pharmaceutical composition described above are the same than those that are described in the first part of the specification concerning ligands of NKp44L.

Similarly, for formulating a pharmaceutical composition according to the present invention, the one skilled in the art will refer to the first part of the specification concerning ligands of NKp44L.

The invention concerns also a pharmaceutical composition for treating a cancer, which comprises an effective amount of a polypeptide of formula (I), fused to a targeting cancer cells, in combination with at least one physiologically acceptable excipient.

Preferably, said compound, which targets cancer cells, consists of an antibody directed to an antigen specific of cancer, such as SCP-1, NY-ESO-1, or SSX-2 specific of breast cancer, SSX-2, NY-ESO-1, or MAGE-3 specific of melanoma, described in U.S. Pat. No. 6,338,947; or antigens specific of renal cancers such as those described in U.S. Pat. No. 6,440,663; KH-1 and N3 specific of colon cancer, described in U.S. Pat. No. 6,238,668.

The present invention is further illustrated by, without in any way being limited to, the following examples.

EXAMPLES

A. Material and Methods of the Examples 1-5

A.1 HIV-1 Infected Donors.

Blood samples of 25 HIV-1-infected patients were obtained from consenting donors at Hôpital Pitié-Salpétrière. Bio-clinical examinations included routine determinations of the viral load, total blood and CD4+ T lymphocyte counts.

As control group, Blood samples from 20 uninfected donors were obtained by leukapheresis from the blood bank (Hôpital Pitié-Salpétrière).

A.2 Cytofluorometric Analysis

A three-colors FACS analysis was performed on freshly harvested PBMC. Isotype-matched immunoglobulin served as the negative control (BD). Cells were incubated 1 h at 4° C., with the appropriate cocktail of antibodies. Anti-CD3; anti-CD4; anti-CD8, anti-CD56, anti-NKp44, anti-NKp46 or anti-NKp44L mAb. Erythrocytes were lysed using the FACS lysing solution (BD). A minimum of 20,000 leucocytes was analyzed on a FACScan, as previously described.

To measure the expression of cell surface activation markers, PBMC were stained with PE- or FITC-conjugated anti-HLA-DR, anti-CD69, anti-CD25, or anti-CD71 (all from BD) and analyzed by FACS.

A.3 Purification of T CD4+ Cells Expressing NKp44L

CD4+ T cell subset sorting was performed using the RosetteSepCD4+ enrichment kit (StemCell). CD4+ T expressing NKp44L were positively selected by a two step magnetic separation, CD4+ T cells were incubated with 10 g/ml of anti-NKp44L for 1-h at RT, followed by treatment with goat anti IgM mouse-coated Dynabeads (Dynal) at a bead-to-cell ratio of 10:1 for 30 min at RT. The cell fraction purity was determined by FACS analysis.

A.4 Isolation of Primary NK Cells and NK Cytotoxicity Assays.

NK lines were generated from PBMC, and then purified using the StemSep cell separation system and the NK cell enrichment antibody cocktail (StemCell technologies). NK purified cells were cultured in MyeloCult H5100 medium (StemCell technologies) supplemented with 100 units rhIL-2 (Boheringer). The purity of these preparations was evaluated by flow cytometry after staining with anti-CD3 (BD), anti-CD56 (BD), anti-NKp44, and anti-NKp46 mAbs.

The cytolytic activity was assayed in 4-h $^{51}$Cr-release assay as previously described. Briefly, the target cells were labeled for 2-h at 37° C. with 100 µCi per $10^6$ cells Na$^{51}$Cr (Amersham), and washed twice with culture medium. The target cells were then distributed in round-bottomed 96-well microtiter plates ($4 \times 10^3$ cells per well), and the effector cells were added at several E/T ratio. The plates were incubated 4-h at 37° C. The supernatant were then collected and $^{51}$Cr-release was measured in a gamma counted. In experiments in which Abs were included, these were added to final concentration of 20 µg/ml. The relative specific $^{51}$Cr-release was calculated according to conventional methods. Values for spontaneous $^{51}$Cr-release, which are deducted in the calculation, were between 10 and 20% of the total incorporated radioactivity. The results are presented after subtraction of the nonspecific lysis obtained with control targets. Each point represents the average of triplicate values. The range of the triplicates was always within 5% of their mean.

A.5 Statistical Analysis

Correlation analyses were performed using Sperman's non-parametric rank correlation analysis. All calculations were performed using the GraphPad Prism.

B. Material and Methods of the Examples 6-10

B.1 Purification of T CD4+ Cells

CD4+ T cell subset sorting was performed using the RosetteSepCD4+ enrichment kit (StemCell). The cell fraction purity was determined by FACS analysis.

B.2 Cytofluorometric Analysis

A two-colors FACS analysis was performed on purified CD4+ T cells. Isotype-matched immunoglobulin served as the negative control (BD). Cells were incubated 1 h at 4° C., with the appropriate cocktail of antibodies. anti-CD4 or anti-NKp44L mAb. A minimum of 20,000 CD4+ T cells was analyzed on a FACScan, as previously described. The intracellular expression of NKp44L was realized as previously described, briefly, the cells were incubated in 4% PFA buffer for 20 min, then washed in stained in presence of 0.1% saponin/PBS/1% BSA buffer at 4° C. the cells were then analyzed by FACS.

B.3 Isolation of Primary NK Cells and NK Cytotoxicity Assays.

NK lines were generated from PBMC, and then purified using the StemSep cell separation system and the NK cell enrichment antibody cocktail (StemCell technologies). NK purified cells were cultured in MyeloCult H5100 medium (StemCell technologies) supplemented with 100 units rhIL-2 (Boheringer). The purity of these preparations was evaluated by flow cytometry after staining with anti-CD3 (BD), anti-CD56 (BD), anti-NKp44, and anti-NKp46 mAbs.

The cytololytic activity was assayed in 4-h $^{51}$Cr-release assay as previously described. Briefly, the target cells were labeled for 2-h at 37° C. with 100 µCi per $10^6$ cells Na$^{51}$Cr (Amersham), and washed twice with culture medium. The target cells were then distributed in round-bottomed 96-well microtiter plates ($4 \times 10^3$ cells per well), and the effector cells were added at several E/T ratio. The plates were incubated 4-h at 37° C. The supernatant were then collected and $^{51}$Cr-release was measured in a gamma counted. In experiments in which Abs were included, these were added to final concentration of 20 µg/ml. The relative specific $^{51}$Cr-release was calculated as previously described. Values for spontaneous $^{51}$Cr-release, which are deducted in the calculation, were between 10 and 20% of the total incorporated radioactivity. The results are presented after subtraction of the nonspecific lysis obtained with control targets. Each point represents the average of triplicate values. The range of the triplicates was always within 5% of their mean.

B.4 Recombinant Vaccinia Virus Expression HIV-1 Protein.

Purified CD4+ T cells were infected with wild type vaccinia virus (WT) or with the various recombinant vaccinia virus at a multiplicity infection of 20 PFU/cell were used as target cells. Recombinant vaccinia viruses for HIV-1-LAI Gag, Pol, Env, Nef, Tat and Vif proteins were provided by Transgène (Strasbourg, France).

B.5 Peptides and Pools of Peptides.

The synthetic 15-mers peptides were purchased from Epytop (Nîmes, France) or kindly provided by Agence Nationale de la Recherche sur le SIDA. All were more than 80% pure as shown by HPLC profiles. Pools of peptides included around 10 different peptides and each peptide overlap the previous continuous peptide for 11 residues.

C. Results

Example 1

Full Length and Anti-Sense Nkp44L Vectors and Production of Stable Transfectants

The full length vector (pEF6-NKp44L) was obtained by sequential subcloning in the pEF6 vector (Invitrogen) of three overlapping RT-PCR fragments of NKp44L, previously cloned in the PCR-zero-blunt vector (Invitrogen); fragment A: 1 (numbered from the ATG translation site; nucleotides 1-3) to 902; fragment B: 813 to 2066, and fragment C: 1983 to 3507 (containing the Stop TGA translation site). The integrity of the full length sequence was confirmed by sequencing and in vitro transcription/translation assay according to the manufacturer's instructions (STP3 kit, Novagen).

The RNA anti-sense NKp44L vector (pEF6-NKp44L-AS5) was obtained by cloning in the pEF6 vector, fragment A, described above, in the anti-sense orientation. The orientation and the integrity of the sequence were confirmed by sequencing. Ten million 721.221 cells were stably transfected with the pEF6-NKp44L-AS5 vector by electroporation (230 V, 250 µF) and selected in 24 well-plates in presence of 10 µg/ml of blasticidin (Invitrogen). The expression of the pEF6-NKp44L-AS5 construct in 721.221 cells was confirmed by RT-PCR analysis.

Example 2

Preparation of Monoclonal Antibodies

Anti-NKp44 receptor (44/8, IgG1) and anti-NKp44L mAbs (7.1, 7.7 and 7.13) were produced in BALB/c mice, immunized three times with NKp44-1 g, or with NKp44L-(HIS)6Tag recombinant proteins, respectively, using the ClonaCell-HY hybridoma cloning kit, according to the manufacturer's instructions (StemCell Technologies Inc.). Antibodies were selected by ELISA based on reactivity with recombinant proteins, using the anti-mouse-peroxidase hybridoma screening reagent (Roche), as well as FACS analysis. NKp44L-(His)6Tag recombinant protein was produced in COS-7 cells. The mammalian expression vector (pcDNA3/V5-HIS-tag; Invitrogen) encoded a string of six histidine residues contained a fragment of NKp44L coding for the 169 C-terminal amino acids, obtained by the yeast two-hybrid system. Recombinant NKp44L protein was purified using a nickel affinity column under native condition (Xpress system protein purification, Invitrogen). Several anti-NKp44L mAbs were obtained: 7.1 (IgM), which is effective for the detection by FACS analysis, and 7.7 (IgM) and 7.13 (IgM) were capable of immunoprecipitation, immunoblotting and immunostaining. Anti-NKp44 mAb (44/8) was purified on a Poros G20 AL protein G column in the High Pressure Perfusion Chromatography Station, as previously described (Malik and Strominger, 1999), and the IgM anti-NKp44L mAbs were purified on a mannan binding protein (MBP) column (Pierce), after ammonium sulfate precipitation (50% saturated solution). The purity of the purified mAbs was confirmed on SDS PAGE.

Example 3

Expression of NKp44L in CD4+ T Cells from HIV-Infected Individuals is Associated with Disease Stage

FIG. 1A) shows the specific expression of NKp44L on CD4+ T cells in HIV-1 infected patients. Comparison between uninfected (Control, open symbols) and HIV-infected (closed symbols) groups. The horizontal lines mark the mean value.

FIG. 1B) shows the inverse correlation of NKp44L expression in CD4+ T cells with peripheral blood CD4 cell count in HIV-infected patients. The correlation (r) and this statistical significance (P) obtained using the Sperman's non-parametric rank correlation test is shown.

FIG. 1C) shows the correlation between NKp44L expression in CD4+ T cells and viral load. The correlation (r) and this statistical significance (P) obtained using the Sperman's non-parametric rank correlation test is shown.

FIG. 1D) shows the over-expression of NKp44L in CD4+ T cells from HIV-infected individuals after PHA activation. Comparison between 5 uninfected (Control, open symbols) and 5 HIV-infected (closed symbols) patients. NA: Non-activated cells; PHA: PHA-activated cells.

Example 4

Expression of NKp44 on CD3-CD56+NK Cells from HIV-Infected Patients

The proportion of NK cells which expressed NKp44 was significantly higher in the HIV-infected individuals with less than 500 CD4+ cells/mm$^3$ than the uninfected cells (control).

Example 5

Higher NK-Lysis Sensitivity of CD4+ T Cells Expressing NKp44L from HIV-Infected Patients

NK92 NK line was analyzed for cytotoxic activity against two purified CD4+ T cells (FIG. 3A) expressing (circle) or not (square) NKp44L. Cytotoxic activity was partially blocked after treatment with anti-NKp44L mAb (a44).

Cytotoxic activity of two IL-2-activated autologous (auto) NK primary cells against purified CD4+ T cells (FIG. 3B) expressing (circle) or not (square) NKp44L, and K562 (star), as positive control for cytotoxic activity.

Cytotoxic activity of unactivated autologous (auto) NK primary cells against two purified CD4+ T cells (FIG. 3C) expressing (circle) or not (square) NKp44L, and K562 (star), as positive control for cytotoxic activity.

Example 6

Effects of Several HIV Viral Proteins on NKp44L Expression

The effect of HIV viral protein on NKp44L expression was examined using infection with recombinant vaccinia virus expressing HIV viral protein. As show in FIG. 4, the expression of NKp44L was markedly enhanced in CD4+ T cells infected with vaccinia virus expressing the gp160 (33.9%) or the gp41 HIV Env proteins (35.6%). In contrast, neither other HIV proteins tested, like Gag, Pol, Tat, nef, vif, or gp120, influenced the cell surface expression of NKp44L protein. Furthermore, the role of the Env protein to enhance the expression of NKp44L was confirmed in a non-viral system. Purified CD4+ T cells were treated with recombinant gp160 protein provided of two different origins, and as shown in FIG. 5A, these gp160 recombinant proteins influenced the expression of NKp44L. Indeed, 10.7% and 9.6% of CD4+ T cells expressed NKp44L after treatment with the gp160-A and gp160-B, respectively. On the other hand, no effect was observed with untreated cells or cells incubated with a control protein. All together, these results show that the recombinant gp160 protein markedly enhances the cell surface expression of NKp44L on CD4+ T-cells surface.

Example 7 gp160 Induces the NK Lysis of CD4+ T Cells

Comparison of NK lysis activity from the untreated cells, the cells treated with the control protein or the cells treated with the both recombinant gp160 proteins (FIG. 5B), shows that target cell lysis was increased in the presence of CD4+ T cells cultured with recombinant gp160 protein. The use of two different types of recombinant gp160 proteins indicates that the procedure used to induce over-expression of NKp44L and increased of NK lysis activity had no influence on the outcome of the experiments. Together, these results indicate that gp41 HIV Env protein was required for the over-expression of NKp44L correlated with a strong increased of NK lysis activity.

Example 8

Identification of the Peptide Motif of the gp41 Env Protein Involved in the Increased of NK Lysis Activity The effect of pool of overlap peptides prepared, as described in the Materials & Methods section, has been tested, to include all of the gp41 protein. CD4+ T cells were incubated with 5 µg of each pool of peptides and tested against activated NK cells. As shown in FIG. 6A, NK lysis was increased in cells incubated with the pool of peptides named gp41C, but not with all of the other pool of peptides. The expression of NKp44L in purified CD4+ T cells treated with each of the pool of peptides has been tested. This receptor was only detectable in cells treated with pool gp41C, and the percentage of positive cells was 13.3%. In no instance, NKp44L was detected on the cells incubated with the other pool of peptides tested. This suggested that one or several peptide motifs included in the pool gp41C was directly implicated in the increased of NK lysis via the over-expression of NKp44L. Repeated experiments with all of the peptides included in the pool gp41C was then tested. As shown in FIG. 7A, the NK cytotoxic activity was strongly increased in presence of the peptides gp41-C145, 41-C146, and 41-C147. By contrast, with the other peptides tested, the NK lysis activity remained low, close to the background. In parallel, the expression of NKp44L was increased after pretreatment of CD4+ T cells with the peptides gp41-C145, gp41-C146, and gp41-C147, with a percentage of positive cells varied between 22 and 16%, but not with the other peptides (less than 7% of positive cells) (FIG. 7B). These results indicated that a peptide specific to gp41 Env HIV protein could increased a NK lysis activity. Additional support to this conclusion come from that the continuous peptides named gp41-C145, gp41-C146, and gp41-C147 included a common peptide motif NH2-SWSNKS—COOH (SEQ ID NO: 7). This motif specific to the gp41 HIV-1 protein was strongly conserved. After having shown that some continuous peptides of the gp41 are some major mediators of NK lysis, it was important to assess if the peptide motif NH2-SWSNKS—COOH (SEQ ID NO: 7) was directly implicated in the NK lysis of CD4+ T cells. Preliminary experiment with this 6-mers peptide shown any increased of cell surface expression of NKp44L or NK cytotoxic activity, suggesting that this sequence is too small or too rapidly attack by some peptidases. However, to test this hypothesis, two 15-mers peptides derived from gp41-C146 (WT) included some mutation inside the NH2-SWSNKS—COOH (SEQ ID NO: 7) motif (CtI1) or in all of the 15-mers sequence (CtI2) have been constructed (FIG. 8A). As shown in FIG. 8B, the NK cytotoxic activity was strongly increased in presence of the peptide WT. By contrast, with untreated cells (none) or the treated with the both control peptides. Similar pattern was observed concerning the cell surface expression of NKp44L, indeed, in cells treated with the WT peptide, approximately 17.4% of CD4 T cells expressed this marker. By contrast, the percentage of NKp44L+ cells was less than 4% in untreated cells or cells treated by the control peptides. These results show that the NH2-SWSNKS—COOH (SEQ ID NO: 7) motif included in the gp41 protein is strongly implicated in the NK lysis of CD4+ T cells.

The effect of gp41 peptide is time dependant (FIG. 9). NK lysis activity started after 30 min of incubation with the WT peptide and approached a maximum closed to 4-days. On the other hand, no significant effect is observed after treatment with the untreated cells or the cells treated with the control peptides. Furthermore, the increased of NK lysis activity is strongly inhibited after pretreatment of cells with anti-NKp44L mAb, confirming that the NK activity is directly correlated with an increase of cell surface expression of NKp44L, in cells treated with the WT peptide (FIG. 9C). However, kinetic study of the cell surface expression of NKp44L revealed that this receptor was rapidly expressed at the cell surface, indeed after 10 min of treatment with WT peptide, around 10% of CD4+ T cells expressed this protein, and the maximum of expression (approximately 30%) was obtained 4-days after treatment. The very fast cell surface expression of NKp44L suggested an absence of new synthesis of NKp44L, and suggested that this protein was present inside the CD4+ T cells cultured with IL2. This hypothesis was confirmed by an intracellular staining of NKp44L. As show in FIG. 9D, high expression of NKp44L was detectable inside the cells, and this independently of the presence of peptides.

Example 9

Cell Surface Expression of NKp44L of Different Human Cells

As shown on FIG. 10, the surface expression of NKp44L on K562, Jurkat, and resting PBMC has been tested. The cells were incubated with 1 µg/ml of anti-NKp44L mAb anti-NKp44L mAb (grey thick line) or with the IgM isotype control (black thin), and analyzed by flow cytometry. It is clearly shown that, contrary to PBMC, tumor cells, like jurkat, and K562 cells express NKp44L on their surface.

REFERENCES

Ameisen J C, Capron A. Cell dysfunction and depletion in AIDS: the programmed cell death hypothesis. Immunol Today 1991; 12(4):102-5.
Bagnarelli P, Menzo S, Valenza A, Manzin A, et al. Molecular profile of human immunodeficiency virus type 1 infection in symptomless patients and in patients with AIDS. J Virol 1992; 66(12):7328-35.
Cantoni C, Bottino C, Vitale M, Pessino A, Augugliaro R, Malaspina A, Parolini S, Moretta L, Moretta A, Biassoni R., 1999, NKp44, a triggering receptor involved in tumor cell lysis by activated human natural killer cells, is a novel member of the immunoglobulin superfamily, J Exp Med 1999 Mar. 1; 189(5):787-96

CDC. 1993 revised classification system for HIV infection and expanded surveillance case definition for AIDS among adolescents and adults. MMWR 1992; 41:1-19.

CDC. Revision of the surveillance case definition of acquired immunodeficiency syndrome. MMWR 1987; 36:3S-15S.

Clark S J, Saag M S, Decker W D, Campbell-Hill S, et al. High titers of cytopathic virus in plasma of patients with symptomatic primary HIV-1 infection. N Engl J Med 1991; 324(14):954-60.

Coombs R W, Collier A C, Allain J P, Nikora B, et al. Plasma viremia in human immunodeficiency virus infection. N Engl J Med 1989; 321 (24):1626-31.

Edwards and Leatherbarrow, 1997, Analytical Biochemistry, 246: 1-6.

Embretson J, Zapancic M, Ribas J L, Burke A, et al. Massive covert infection of helper T lymphocytes and macrophages by HIV during the incubation period of AIDS. Nature 1993; 362(6418):359-62.

Fauci A S. Multifactorial nature of human immunodeficiency virus disease: implications for therapy. Science 1993a; 262 (3136):1011-8.

Felici F., 1991, J Mol Biol, 222:301-310.

Finkel T H, Tudor-Williams G, Banda N K, et al. Apoptosis occurs predominantly in bystander cells and not in productively infected cells of HIV- and SIV-infected lymph nodes. Nature Medicine 1995; 1 (2):129-34.

Fox C H, Kotler D, Tierney A, Wilson C S, Fauci A S. Detection of HIV-1 RNA in the lamina propria of patients with AIDS and gastrointestinal disease. J Infect Dis 1989; 159 (3):467-71.

Garry R F. Potential mechanisms for the cytopathic properties of HIV. AIDS 1989; 3(11):683-94.

Golding H, Shearer G M, Hillman K, Lucas P, et al. Common epitope in human immunodeficiency virus I (HIV) I-GP41 and HLA class II elicits immunosuppressive antibodies capable of contributing to immune dysfunction in HIV-infected individuals. J Clin Invest 1989; 83(4):1430-5.

Gong et al., 1994, Leukemia, vol. 8 (4):652-658.

Ho D D, Moudgil T, Alam M. Quantitation of human immunodeficiency virus type 1 in the blood of infected persons. N Engl J Med 1989; 321 (24):1621-5.

Ho D D, Neumann A U, Perelson A S, Chen W, et al. Rapid turnover of plasma virions and CD4 lymphocytes in HIV-1 infection. Nature 1995; 373:123-6.

Hoxie J A, Alpers J D, Rackowski J L, Huebner K, et al. Alterations in T4 (CD4) protein and mRNA synthesis in cells infected with HIV. Science 1986; 234(4780):1123-7.

Hugin A W, Vacchio M S, Morse H C III. A virus-encoded superantigen in a retrovirus-induced immunodeficiency syndrome of mice. Science 1991; 252(5004):424-7.

Janeway C. Immune recognition. Mls: makes little sense. Nature 1991; 349(6309):459-61.

Koenig S, Earl P, Powell D, Pantaleo G, et al. Group-specific, major histocompatibility complex class-I restricted cytotoxic responses to human immunodeficiency virus I (HIV-1) envelope proteins by cloned peripheral blood T cells from an HIV-1 infected individual. Proc Natl Acad Sci USA 1988; 85(22):8638-42.

Koga Y, Lindstrom E, Fenyo E M, Wigzell H, Mak T W. High levels of heterodisperse RNAs accumulate in T cells infected with human immunodeficiency virus and in normal thymocytes. Proc Natl Acad Sci USA 1988; 85(12): 4521-5.

Kohler G. and Milstein C., 1975, Nature, 256: 495.

Kozbor et al., 1983, Hybridoma, 2(1): 7-16.

Laurent-Crawford A G, Krust B, Muller S, Riviere Y, et al. The cytopathic effect of HIV is associated with apoptosis. Virology 1991; 185(2):829-39.

Leblanc V, Delaunay V, Claude Lelong J, Gas F, Mathis G, Grassi J, May E. 2002. Anal Biochem. 2002 September 15; 308(2):247-54.)

Leger O J et al., 1997, Hum Antibodies, 8(1): 3-16.

Leonard R, Zagury D, Desportes I, Bernard J, et al. Cytopathic effect of human immunodeficiency virus in T4 cells is linked to the last stage of virus infection. Proc Natl Acad Sci USA 1988; 85(10):3570-4.

Lifson J D, Reyes G R, McGrath M S, Stein B S, Engleman E G. AIDS retrovirus induced cytopathology: giant cell formation and involvement of CD4 antigen. Science 1986; 232(4754):1123-7.

Lucas A. H., 1994, In: Development and Clinical Uses of Haemophilus b Conjugate.

Lyerly H K, Matthews T J, Langlois A J, Bolognesi D P, Weinhold K J. Human T-cell lymphotropic virus IIIB glycoprotein (gp120) bound to CD4 determinants on normal lymphocytes and expressed by infected cells serves as target for immune attack. Proc Natl Acad Sci USA 1987; 84(13):4601-5.

Martineau P., Jones P., Winter G., 1998, J Mol Biol, 280(1): 117-127.

Michael N L, Vahey M, Burke D S, Redfield R R. Viral DNA and mRNA correlate with the stage of human immunodeficiency virus (HIV) type 1 infection in humans: evidence for viral replication in all stages of HIV disease. J Virol 1992; 66(1):310-6.

Muro-Cacho C A, Pantaleo G, Fauci A S. Analysis of apoptosis in lymph nodes of HIV-infected persons. Intensity of apoptosis correlates with the general state of activation of the lymphoid tissue and not with stage of disease or viral burden. J Immunol 1995; 154(10):5555-66.

Oldenburg K. R. et al., 1992, Proc. Natl. Acad. Sci. USA, 85(8): 2444-2448.

Pantaleo G, Fauci A S. Apoptosis in HIV infection. Nature Medicine 1995b; 1 (2):118-20.

Pantaleo G, Graziosi C, Demarest J F, Butini L, et al. HIV infection is active and progressive in lymphoid tissue during the clinically latent stage of disease. Nature 1993b; 362(6418):355-8.

Pantaleo G, Graziosi C, Fauci A S. The immunopathogenesis of human immunodeficiency virus infection. N Engl J Med 1993a; 328(5):327-35.

Parmley and Smith, 1988, Gene, 73: 305-318.

Pauza C D, Galindo J E, Richman D D. Reinfection results in accumulation of unintegrated viral DNA in cytopathic and persistent human immunodeficiency virus type 1 infection of CEM cells. J Exp Med 1990; 172(4):1035-42.

Piatak M Jr, Saag M S, Yang L C, Clark S J, et al. High levels of HIV-1 in plasma during all stages of infection determined by competitive PCR. Science 1993; 259(5102):1749-54.

Popovic M, Sarngadharan M G, Read E, Gallo R C. Detection, isolation and continuous production of cytopathic retroviruses (HTLV-III) from patients with AIDS and pre-AIDS. Science 1984; 224(4648):497-500.

Reinmann K A et al., 1997, AIDS Res Hum Retroviruses, 13(11): 933-943.

Ridder R., Scmitz R., Legay F., Gram H., 1995, Biotechnology (N Y), 13(3): 255-260.

Schnittman S M, Denning S M, Greenhouse J J, Justement J S, et al. Evidence for susceptibility of intrathymic T-cell precursors and their progeny carrying T-cell antigen receptor phenotypes TCR alpha beta+ and TCR gamma delta+ to human immunodeficiency virus infection: a mechanism for CD4+ (T4) lymphocyte depletion. Proc Natl Acad Sci USA 1990b; 87(19):7727-31.

Sodroski J, Goh W C, Rosen C, Campbell K, Haseltine W A. Role of the HTLV-III/LAV envelope in syncytium formation and cytopathicity. Nature 1986; 322(6078):470-4.

Stanley S K, Kessler S W, Justement J S, Schnittman S M, et al. CD34+ bone marrow cells are infected with HIV in a subset of seropositive individuals. J Immunol 1992; 149 (2):689-97.

Szabo et al., 1995, Curr. Opinion Struct. Biol., 5(5): 699-705.

Terai C, Kornbluth R S, Pauza C D, Richman D D, Carson D A. Apoptosis as a mechanism of cell death in cultured T lymphoblasts acutely infected with HIV-1. J Clin Invest 1991; 87(5):1710-5.

Valadon P. et al., 1996, J Mol Biol, 261: 11-22.

Vitale M, Bottino C, Sivori S, Sanseverino L, Castriconi R, Marcenaro E, Augugliaro R, Moretta L, Moretta A., 1998, NKp44, a novel triggering surface molecule specifically expressed by activated natural killer cells, is involved in non-major histocompatibility complex-restricted tumor cell lysis, J Exp Med 1998 Jun. 15; 187(12):2065-72

Wei X, Ghosh S K, Taylor M E, Johnson V A, et al. Viral dynamics in human immunodeficiency virus type 1 infection. Nature 1995; 373:117-22.

Westerink M. A. J., 1995, Proc. Natl. Acad. Sci. USA, 92: 4021-4025.

Zagury D, Bernard J, Leonard R, Cheymier R, et al. Long-term cultures of HTLV-III infected T cells: a model of cytopathology of T-cell depletion in AIDS. Science 1986; 231(4740):850-3.

The invention claimed is:

1. A purified antibody directed to the extracellular domain portion of NKp44L protein of SEQ ID NO: 1.

2. The antibody of claim 1, further defined as a polyclonal antibody, a monoclonal antibody, or a single chain Fv antibody fragment.

3. A composition comprising the antibody of claim 1.

4. The composition of claim 3, further comprising a marker molecule that specifically binds to the CD4 antigen.

5. The composition of claim 3, further comprising one or more physiologically acceptable excipient.

* * * * *

UNITED STATES PATENT AND TRADEMARK OFFICE
CERTIFICATE OF CORRECTION

| | | |
|---|---|---|
| PATENT NO. | : 8,372,955 B2 | Page 1 of 1 |
| APPLICATION NO. | : 11/927400 | |
| DATED | : February 12, 2013 | |
| INVENTOR(S) | : Vieillard et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this
Fourth Day of November, 2014

Michelle K. Lee
*Deputy Director of the United States Patent and Trademark Office*